(12) United States Patent
Akin et al.

(10) Patent No.: US 7,745,189 B2
(45) Date of Patent: Jun. 29, 2010

(54) REGULATABLE GROWTH OF FILAMENTOUS FUNGI

(75) Inventors: Ali R. Akin, Berkeley, CA (US); Elizabeth A. Bodie, San Carlos, CA (US); Shirley M. Burrow, Preston (GB); Nigel Dunn-Coleman, Tenerife (ES); Geoffrey Turner, Sheffield (GB); Michael Ward, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 12/184,211

(22) Filed: Jul. 31, 2008

(65) Prior Publication Data

US 2009/0093039 A1    Apr. 9, 2009

Related U.S. Application Data

(63) Continuation of application No. 10/100,252, filed on Mar. 14, 2002, now Pat. No. 6,936,449.

(60) Provisional application No. 60/276,571, filed on Mar. 15, 2001, provisional application No. 60/276,618, filed on Mar. 14, 2001.

(51) Int. Cl.
    *C12N 9/12*     (2006.01)
    *C12N 15/00*    (2006.01)
    *C12P 21/06*    (2006.01)
    *C12P 19/34*    (2006.01)
    *C07H 21/04*    (2006.01)

(52) U.S. Cl. .................. 435/194; 435/69.1; 435/91.1; 435/320.1; 536/23.2

(58) Field of Classification Search .................. None
See application file for complete search history.

(56) References Cited

U.S. PATENT DOCUMENTS 4,816,567 A    3/1989    Cabilly et al.
6,291,665 B1    9/2001    Gaffney et al.

FOREIGN PATENT DOCUMENTS

| EP | 1 384 782 A1 | 1/2004 |
|---|---|---|
| WO | WO 00/56762 A2 | 9/2000 |
| WO | WO 01/71042 A2 | 9/2001 |
| WO | WO 02/16439 A2 | 2/2002 |
| WO | WO 02/079476 | 10/2002 |
| WO | WO 02/086090 A2 | 10/2002 |
| WO | WO 03/016475 A2 | 2/2003 |

OTHER PUBLICATIONS

Broun et al., Catalytic plasticity of fatty acid modification enzymes underlying chemical diversity of plant lipids. Science, 1998, vol. 282: 1315-1317.*

Seffernick et al., Melamine deaminase and Atrazine chlorohydrolase: 98 percent identical but functionally different. J. Bacteriol., 2001, vol. 183 (8): 2405-2410.*

Witkowski eta l., Conversion of b-ketoacyl synthase to a Malonyl Decarboxylase by replacement of the active cysteine with glutamine. Biochemistry, 1999, vol. 38: 11643-11650.*

Altschul, Stephen F., et al., "Basic Local Alignment Search Tool," *J. Mol. Biol.*, 215:403-410 (1990).

Altschul, Stephen F. et al., "Gapped Blast and PSI-Blast: a new generation of protein database search programs," *Nucleic Acids Research*, 25(17):3389-3402 (1997).

Buhr, T. L., et al., "A kinase-encoding gene from *Collectorichum trifolii* complements a colonial growth mutant of *Neurospora crassa*," *Mol. Gen. Genet.*, 251:565:572 (1996).

Carter, Paul et al, "Improved oligonucleotide site-directed mutagenesis using M13 vectors," *Nucleic Acids Research*, 13(12):4431-4443 (1985).

Collinge, Annette J. et al., "Physiology and Cytology of Septation and Branching in a Temperature-Sensitive Colonial Mutant, (cot 1) of *Neurospora Crassa*," *Trans. Br. mycol. Soc.*, 71 (1) pp. 107-120, 1978.

Cordonnier-Pratt, M.—M. et al., Database EMBL Sorghum bicolor EST, Jul. 21, 2000, XP002317681, Database accession No. AW565013.

Deutscher Murray P., "Rethinking Your Purification Procedure," *Methods in Enzymology*, vol. 182, pp. 779-780, 1990.

Durrenberger, F. et al., "The ukcl gene encodes a rotein kinase involved in morphogenesis, pathogenicity and pigment formation in *Ustilago maydis*," *Molecular and General Genetics*, 261(2):281-289, XP002303546 (1999).

Gorovits, Rena et al., "A Mutation within the Catalytic Domain of COT1 Kinase Confers Changes in the Presence of Two COT 1 Isoforms and in Ser/Thr Protein Kinase and Phosphatase Activities in *Neurospora crassa*," *Fungal Genetics and Biology, Academic Press*, vol. 27, pp. 264-274, 1999.

Kohler, G., et al., "Continuous cultures of fused cells secreting antibody of predefined specificity," *Nature*, vol. 256, pp. 495-497, Aug. 7, 1975.

Lauter, Frank-Roman et al., Photoregulation of *cot-1*, a Kinase Encoding Gene Involved in Hyphas Growth in *Neurospora crassa*, *Fungal Genetics and Biology*, 23:300-310 (1998).

Murray, Elizabeth E. et al., "Codon usage in plant genes," *Nucleic Acids Research*, vol. 17, No. 2, pp. 477-498, 1989.

(Continued)

*Primary Examiner*—Ganapathirama Raghu

(57) ABSTRACT

The present invention generally relates to hyphal growth in fungi and in particular describes the modulation of genes associated with hyphal growth in filamentous fungi. The present invention provides methods and systems for the production of proteins and/or chemicals from filamentous fungi which comprise modulation of genes associated with hyphal growth. Specifically, the present invention is directed to a full length cotA gene, its gene product and methods of use.

6 Claims, 14 Drawing Sheets

OTHER PUBLICATIONS

Pollerman, S. et al., "Control of hyphal morphology in *Aspergilus niger* by regulated expression of the cotA gene," Online Mar. 16, 2001, XP002303544.

Scopes, Protein Purification: Principles and Practice, Springer-Verlag, New York, New York, 1982.

Steele, Graham C. et al., "Effect of Temperature and Temperature Shifts on Growth and Branching of a Wild Type and a Temperature Sensitive Colonial Mutant (Cot1) of *Neurospora crassa*," *Archives of Microbiology*, vol. 113, pp. 43-48, 1977.

Ward, Michael et al., "Use of *Aspergillus* overproducing mutants, cured for integrated plasmid, to overproduce heterologous proteins," *Applied Microbiology and Biotechnology*, vol. 39, pp. 738-743, Springer-Verlag, 1993.

Wells, J.A., et al., "Importance of hydrogen-bond formation in stabilizing the transition state of subtilisin," Phil. Trans. R. Soc. Lond., 317, pp. 415-423, 1986.

Yarden, O. et al., "*cot-1*, a gene required for hyphal elongation in *Neurospora crassa*, encodes a protein kinase," *The EMBO Journal*, 11(6):2159-2166 (1992).

Zoller, Mark J. et al., "Oligonucleotide-directed mutagenesis using M13-derived vectors, : an efficient and general procedure for the production of point mutations in any fragment of DNA," *Nucleic Acids Research*, vol. 10, No. 20, pp. 6487-6500, 1982.

\* cited by examiner

```
TTTCCATCAT GGATCCCAAC AACAACAACC GACTCCACCT GAATTTCGGG    50
TACAATGATC GTGGTTTCAA TGCGGCGGCG GCCAACAACC GCGCCTATCC   100
CACTACCCCC TCCGCCTTCC CCCAGCCGAT CTACCAAAAC CAGGGTCCCC   150
AGGATTACAT GGACGCCCAG AACGGTGCCT ACGCTCAAGG TGGTTATTTC   200
ATGGCCAATC CTTACCAAGC TCAGGCAGCC TACGGCCAGC CGCATTATGG   250
CCAGAACCTG CAGTCCCTC AGCCCGCCTA CCCATCCCGC ATGGGTTACA   300
GCGCGAACGA TGGCACCAAC GGTTTGATCC AGCAGTTCTC GAACCAGGAT   350
CTGAATTCCC CTCGCTCGGG TTTCTTTGCT CGTTCTGCCT CGCCAGCCCA   400
GCGACCCCGA ACTGCCGGCT CCCCCGCCCC CGGGCAGCAA CAGCCAGGCC   450
ACCTGGCGCC TCCTATGCCT CGTAGCCCTC GCACCCCCGC GGAGAACGAA   500
GAGTTGCAAC GGTACCCGGA ACGTTACTCA GAGAATGTTC ACAAGCGTGG   550
CAAGGCAGCC AAGGAGCTGG TCAGCGTCTT CTTAATGAGA ACAATGAGCG   600
CGCACGCGAT CGCAACATGC GGTGAGTATT CCACACAATG CCACGGCCTC   650
CCTCCCAACC CAACAGGGAA TTTGGTATCG CTGACTCGGG TGCTTTTCAT   700
AGGTCTGCTG AGCTGGACAA GATGATCCGT GAACCCAGTA TTCCCAAGGA   750
GAACAAGTGC AAGGACGCAG AGGTGCTTGC TAAGAAGGAA TCGAATTTCC   800
TCCGGTTCCT TCGCACCAAG GAGACCCCGC AGAACTTCCA GACCATCAAG   850
ATCATCGGAA AGGGCGCGTT TGGTGAAGTG AAGCTGGTAC AACGGAAGGC   900
CGATGGCAAG ATTTACGCAC TGAAGTCGTT GATCAAAACG GAGATGTTCA   950
AGCAAGGACC AGCTGCTCAC GTTCGCGCGG AACGTGATAT CCTTGCTGAT  1000
TCCAAGGACA ACCCGTGGTT GGTGAAGCTG CATGCTTCTT TCCAGGACAC  1050
TGCCTACTTG TATTTGCTGA TGGAATTCTT GCCTGGTGGT GACTTGATGA  1100
CCATGTTGAT CAAGTACGAG ATCTTCTCCG AGGATATCAC TCGGTTCTAT  1150
ATGGCCGAAA TTGTCATGGC GATCGAGGCT GTTCACAAGC TCGGCTTCCT  1200
TCACCGGGAC ATCAAGCCTG ATAACATCCT TCTGGATCGC GGTGGTCACG  1250
TCAAGCTGAC GGACTTTGGT CTGTCCACGG AGGAAAGAA GACCCACGAC  1300
AACTCCTACT ATCAGAATCT GCTGAAGAAC TCGACGTCAA AGGACAAGAA  1350
CCGCAACTCT GGTTACTTCA ACGATGCGAT CAACCTGACA GTCTCCAACC  1400
GTGGCCAGAT CAACACCTGG AGAAAGTCTC GTCGTGCAAT GGCATACTCG  1450
ACGGTCGGAA CTCCGGACTA TATCGCCCCC GAGATCTTCA ACGGCCAAGG  1500
ATACACCTAC CTGTGCGATT GGTGGTCTGT AGGTGCTATC ATGTTCGAGT  1550
GCCTTGTGGG TTGGCCCCCG TTCTGCGCGG AAGACACCAC CGACACCTAC  1600
CGCAAGATTG TGAACTGGAG AGAATGCTTG TACTTCCCTG AGGAACTCAC  1650
CCTTTCGCGC GATTCCGAGG GTCTCATCCG AAGGTAAGCT TGAAGCCGAG  1700
AAGCGTGAGG CCAGAAAGGC CGCAAGCACG AAGAACATTG ACGGAGAAGT  1750
GAAGAAGGAA GACTCTGACC CACTAGGCAA CCAG                   1784

Figure 1: DNA sequence of truncated A. niger cotA (SEQ ID NO:1)
```

FIG. 1

```
MEPNNNNRLH LNFGYNDRGF NAAAANNRAY PTTPSAFPQP    40
IYQNQGPQDY MDAQNGAYAQ GGYFMANPYQ AQAAYGQPHY    80
GQNLQSPQPA YPSRMGYSAN DGTNGLIQQF SNQDLNSPRS   120
GFFARSASPA QRPRTAGSPA PGQQQPGHLA PPMPRSPRTP   160
AENEELQRYP ERYSENVHKR GKAAKELVSV FFNENNERAR   200
DRNMRSAELD KMIREPSIPK ENKCKDAEVL AKKESNFLRF   240
LRTKETPQNF                                    250

Figure 2: Amino acid sequence of truncated A. niger cotA
(SEQ ID NO:2)
```

FIG. 2

*cotA* nucleic acid sequence from *A. nidulans*

```
CGGGATAGGG CTCGGAAAAG CGAGGGCTTC AGAGCATAAG AACATCATCA
GAAAGTGGAG CTTTCGTAGC ACAGTGTCGT GAGGTCCGTC TGATATGGCC
CTGAAAAGTA AGCGTAGTGA GTGGGATGCT CTTCTCGCTT TTGAACATGA
CCGTGACTCT GTCTCAATCC ACACTCAATA CCTTTGTCTC CGTGATATGT
TTCAGATATA GAACCTTAAT GAAGAGCCAA CTTTATGACA AATGCATCTT
CGAGGGGTGG GTGTTGTATA GAGGCAGCGC GGGTGGGCCC CGCGGTCTTC
CGTAGCCCAA CTCCCAAAAC AGTCCAGGGT AACGTACTGG CACCACCGC
ACTGCTTTTA AGCTACTGCT GGTCTTTAAG TCTGGACTCT CGATAACTTG
TTGCGGCTTT GCTTTTCTT TGGTGCTTAT CAACCCAGGT GACTTTGCGA
CCACAGAATC GTTGTCGCTT GCTCAATCGC CTCCTGATCG ATTATCCCTC
TAAGGAGAGC TTGTCCAGTC GGGAGCGCTC CAACACTCCA CTATAGTAAC
ACTGTTCCTT CCCCTCAAGC CGCACTCGCT CACTTGTCTC CTGAAGCCAC
CGCTTCTTCC CACTAACCTT CCCCTCCCCC CTTTACACTT GCACACCCCC
CCCTTATATC CATCACCTTC CTCCATTCCT CATCTCGCCG TCCGTCCAAT
TTTGGTAGTC TGGAGGGCAC TCTTCCAAAA TGGACCCCAA CAACAATCGC
CCCCACCTGA ACTTCGGCTA CAATGAACGT GCCTTCAACC CTGCGGCCGC
AAACAACCGC GCGTATCCCA CCACGCCCTC CGCATTTCCT CAGCCGATCT
ACCAGAGCCA GAGCCCCCAG GACTACATGG ACGCTCAGAA TGGTGTTTAT
GGTCAGGGAT ATTTCATGCC GAACAACTAC CCTGCGCAGG CTGCCTATGC
CCAGCCCCAT TACGGCCAAC CCAATCTCCA GTCTCCTCAG CCCGCCTATC
AGTCTCGAAT GGGATACAAT GTCAGCCCCA ACGATGGAAC AAATGGTTTG
ATACAGCAGT TCTCGAATCA GGATTTAAAC TCGAACCGAA CGGGTTTCTT
CAATCGCTCC GCTTCGCCTG CTCAAAGACC CCGTACTGCA GGCAATACAG
CCCCCGGACA GCAGCAGCAA CCTGGACACT TGGCCCCTCC AGTGCCTCGC
AGCCCTCGGC TGCCCCCCGA GAACGAAGAA CTTCAACGCT ACCCAGAGCG
CTTCTCTGAA AATGTTCACA AACGTGGAAA AGCTGCGAAG GAGTTGGTCA
ACGTATTCTT TCACGAGAAT ATCGAGCGTG CGCGTGATCG CAACATGCGG
TGGGTTTTTG CTACTGAGCG CCGTATTTCT CTAAAAAGAA TTTTGCTAAC
TGGAGTTATA ACTGTACAGT TCGGCGGAGC TCGACAAGAT GATGCGCGAC
CCCAACATTT CACAAGATGC AAAGGTGAAG GAGGCGGAAA TGGTTGGAAA
GAAAGAGTCG ACATTCCTTC GCTTCCTTCG GACACCAGAA ACTCCTGCCA
ACTTCCAAAC CATCAAGATT ATTGGAAAGG GTGCTTTTGG TGAAGTTAAG
CTGGTGCAGA GGAAGTCTGA TAACAAGATC TATGCGCTTA AGTCGCTGAT
```

*FIG. 3A*

```
CAAATCAGAG ATGTTTAAGA AAGATCAGCT CGCCCACGTT CGTGCTGAAC
GTGATATTCT AGCTGACTCG AAGGACAACC CTTGGCTTGT CAAGCTCCAT
GCTTCATTCC AGGATCCCGC ATACCTATAC CTCCTGATGG AGTTCTTACC
TGGAGGTGAT TTGATGACCA TGCTTATTAA GTACGAAATA TTCTCTGAAG
ATATCACACG CTTCTACATG GCGGAAATTG TGATGGCGAT TGAGGCGGTT
CACAAGCTGG GTTTCCTTCA CCGGTGAGAA TAACAATCCT GGTCTCTCGT
ACCATATACA GCGTGCTAAT ATACTTGTAC TATAGAGATA TTAAACCTGA
CAACATCCTT CTCGATCGTG GCGGTCACGT CAAGCTGACC GATTTCGGTC
TCTCAACTGG AGGCAAGAAA ACTCACGACA ACTCATACTA TCAGAACCTG
TTGAAGAATT CAACATCCAA GGATAAGAAC CGAAACTCTG GATACTTCAA
CGATGCTATC AACTTGACAG TATCGAACCG TGGGCAGATC AACACCTGGA
GAAAATCTCG CAGGGCTATG GCTTACTCCA CTGTCGGAAC ACCTGACTAC
ATTGCACCCG AAATTTTTAA TGGTCAAGGA TACACCTATC TTTGCGACTG
GTGGTCCGTC GGTGCCATCA TGTTTGAATG TCTCGTGGGC TGGCCTCCAT
TCTGCGCCGA GGATACGACC GACACCTATC GCAAGATTGT GAACTGGAGG
GAATGCCTAT ATTTCCCCGA AGAATTGACA CTGTCTCGTG AATCGGAGGG
TCTGATTCGA AGGTATGTTA TGTCAGCAAT CCATTTGAGC TGCTTGTCTA
ACCGGAGATC AGCTTCCTAT GTGACGCAGA ACACCGCATC GGCAACGAAG
GTGGCCAATA CGGAGGTGCT ACACAGATCA AAAATCACCC ATTCTTCCGC
GGGGTAGTAT GGGATCAACT GCGCAAAATC CGGGCACCGT TCGAACCCAG
ACTGACGTCA AATATCGACG TATCATATTT CCCGATTGAC GAGATTCCTC
AGGAGGATAC CAGCGCCATT CACCGCGCCC AGGCACGTGC CATGCCGGAT
GAGCAGAATG CTGAGATGAG CCTGCCTTTT ATCGGATACA CATACAAAGC
ATTCAACGCC TTCCAGGCCA GTTGAGCATG CATTTAAAGT AAGAAATATA
TTTGAATGAG CCGATGATGG ATGCCATTGG AAAGTTTTGA AGCGGGCGGG
CTTGCGTTGA TAACTTTTCA ATGGCGCATC CAGGTTTTTG TGTCGGTCGG
CATAGACCCT TGTTGATTGG TATTTTCATC AAGCATATAG CGCATACATC
ATGTCACTGG ACACATGAGC ATCTCACTAC CATATGTG
``` description
cotA sequenced

*FIG. 3B*

| | | | | | |
|---|---|---|---|---|---|
| MDPNNNRPHL | NFGYNERAFN | PAAANNRAYP | TTPSAFPQPI | YQSQSPQDYM | 50 |
| DAQNGVYGQG | YFMPNNYPAQ | AAYAQPHYGQ | PNLQSPQPAY | QSRMGYNVSP | 100 |
| NDGTNGLIQQ | FSNQDLNSNR | TGFFNRSASP | AQRPRTAGNT | APGQQQQPGH | 150 |
| LAPPVPRSPR | LPPENEELQR | YPERFSENVH | KRGKAAKELV | NVFFHENIER | 200 |
| ARDRNMRSAE | LDKMMRDPNI | SQDAKVKEAE | MVGKKESTFL | RFLRTPETPA | 250 |
| NFQTIKIIGK | GAFGEVKLVQ | RKSDNKIYAL | KSLIKSEMFK | KDQLAHVRAE | 300 |
| RDILADSKDN | PWLVKLHASF | QDPAYLYLLM | EFLPGGDLMT | MLIKYEIFSE | 350 |
| DITRFYMAEI | VMAIEAVHKL | GFLHRDIKPD | NILLDRGGHV | KLTDFGLSTG | 400 |
| GKKTHDNSYY | QNLLKNSTSK | DKNRNSGYFN | DAINLTVSNR | GQINTWRKSR | 450 |
| RAMAYSTVGT | PDYIAPEIFN | GQGYTYLCDW | WSVGAIMFEC | LVGWPPFCAE | 500 |
| DTTDTYRKIV | NWRECLYFPE | ELTLSRESEG | LIRSFLCDAE | HRIGNEGGQY | 550 |
| GGATQIKNHP | FFRGVVWDQL | RKIRAPFEPR | LTSNIDVSYF | PIDEIPQEDT | 600 |
| SAIHRAQARA | MPDEQNAEMS | LPFIGYTYKA | FNAFQAS | | 637 |

Figure 4: amino acid sequence of truncated *A. nidulans* cotA (SEQ ID NO:4)

FIG. 4

| | | | | |
|---|---|---|---|---|
| CTGCTGGACC | GTGGCGGCCC | CGTCAAGCTG | ACCGACTTTG | 40 |
| GTCTCTCCAC | GGGCTTCCAC | CGTCTGCACG | ACAACAACTA | 80 |
| CTACCAGCAG | CTGCTGCAGG | GCCGCTCCAA | CCGCCCGCGT | 120 |
| GACCGCACCT | CGGTTGCCAT | TGATCAGATT | AACCTCACAG | 160 |
| TCAGCAACCG | ATCTCAGATT | AACGACTGGA | GACGATCTCG | 200 |
| ACGGCTGATG | GCTTACTCCA | CCGTCGGTAC | ACCAGACTAC | 240 |
| ATCGCCCCNG | AAATTCTCTA | CCTC | | 264 |

Figure 5: *T. reesei* cotA DNA fragment (SEQ ID NO:5)

FIG. 5

| | | | | |
|---|---|---|---|---|
| LLDRGGPVKL | TDFGLSTGFH | RLHDNNYYQQ | LLQGRSNRPR | 40 |
| DRTSVAIDQI | NLTVSNRSQI | NDWRRSRRLM | AYSTVGTPDY | 80 |
| IAPEILYL | | | | 88 |

Figure 6: *T. reesei* cotA amino acid fragment (SEQ ID NO:6)

FIG. 6 cotA and Related Gene

```
Seq. ID No.:
23  spol        1   .........................................................MDPNNNRLHLNFGYNDRGF
17  andcot      1   .........................................................MDP.NNNRPHLNFGYNERAF
18  COT1_NEUCR  1   .........................................................MDNTNRPHLNLGTNDTRM
19  S70706      1   .........................................................MDNNNNRLYLNIGNNNDRL
20  KNQ1_YEAST  1   MYNSSTNHHEGAPTSGHGYYMSQQQDQQHQQQQQQYANEMNPYQQIPRPPAAGFSSNYMKEQGSHQSLQEHLQRETGNLGS 23  spol        21  NAAAANNRAYPTTPSAFPQPIYQNQGPQDYMDAQNGAYAQGGYFM............................ANPYQAQAAYGQPHYGQ
17  andcot      20  NPAAANNRAYPTTPSAFPQPIYQSPQDYMDAQNGVYGQ.GYFM............................PNNYPAQAAYAQPHYGQ
18  COT1_NEUCR  19  .APN.DRTYPTTPSTFPQPVFP...........................................GQQAGGSQQYNQAYAQSGNYY
19  S70706      20  ..GPGSDRQYPTTPSTFPQPVFPHQGQQQQQQQQLHHQQQPGMQHPQQYAQQQQQQQQQPYQTGYAPSGYFN
81  KNQ1_YEAST  81  GFTDVPALNYPATPPPHNNYAASNQMINTPPSMGGLYRHNNNSQSMVQNGSGNAQLPQLSPGQYSIESEYNQNLNGS 23  spol        83  .N...LQSPQPAYPSRMGY..............................SANDGTNGLIQQFSNQDLNSP..RSGFFARSASPAQRPRTAGSPAPG..QQ
17  andcot      81  PN...LQSPQPAYQSRMGYNV.............................SPNDGTNGLIQQFSNQDLNSN..RTGFFNRSASPAQRPRTAGNTAPGQQQ
18  COT1_NEUCR  60  QQ...NH............................................NDPNTGLAHQNIGSAGRASPYGSRGPSPAQRPRTSGNSGQQQ.T
19  S70706      98  PN...QQAAQYPPQGHGDYNAAYQPRSNTFGTNDPNVGLAHQFSHONLGGAARASPYGSRGPSPGQRPRTAGASGQPPSG
20  KNQ1_YEAST  161 SSSSPFHQPQTLRSNGSYSSGLRSVKSFQRLQQEQENVQVQQQLSQAQQQNSRQQQQQLQYQQQQQQQQHMQIQQQQ 23  spol        145 QPGHLAPPMPR.......SPRTPAENEELQRYPE.................RYSENVHKRGKAAKELVSVFFN.ENNE...RAR
17  andcot      147 QPGHLAPPVPR.......SPRLPPENEELQRYPE.................RFSENVHKRGKAAKELVNVFFH.ENIE...RAR
18  COT1_NEUCR  111 YGNYLSAPMPSNTQTEFAPLPSGTPTNMAPMPTTRRSAHSWPLTSLRTASSAPGSATRGECCSDALLPHPAV...IGA.
19  S70706      175 YGHYATPPLPNQQPASVDPFAPAPERNYE.....................KYGPNANGNQKKCTQLASDFFK.DSVK...RAR
22  ORB6_SCHPO  1   ...MDKNDYLHFERNPSL.................................FPKSTLDKVQKTKKYIEHYYKV.AVD...HAV
20  KNQ1_YEAST  241 QQQQQQQQSQSPVQSGFNNGTISNYMYFERRPDL.................LTKGTQDKAAAVKLKIENFYQS.SVK...YAI
21  DMK_HUMAN   1   ............MGGHFWPPEPYTVFMWGSPWEADSPRVKLRGR 23  spol        201 DRNMRSAELDKMIREPSIPKENKCCKDAEVLAKKESNFLRFLRTKETPQNFQTIKIIGKGAFGEVKLVQRKADGKITYALKS
17  andcot      203 DRNMRSAELDKMMRDPNISQDAKVKEAEMVGKKESTFLRFLRTPETPANFQTIKIIGKGAFGEVKLVQRKSDNKITYALKS
18  COT1_NEUCR  188 DTLFRQSEMEQKLGETNDAR..RRESIWSTAGRKEQYLRFLRTKDKPENVQTIKIIGKGAFGEVKLVQKKADGKVTAMKS
19  S70706      233 ERNQRQSEMEAKLSEPNQSQSRREQIWSTAGRKEQYLRFLRTKDKPENINTVKIIGKGAFGEVKLVQKKGDGKVVAMKS
22  ORB6_SCHPO  44  ERNQRRINLEQRLATERGSEERKNRQLRASGEKESQFLRFRRTRLSLEDFSTIKVIGKGAFGEVRLVQKLDTGKIYAMKS
20  KNQ1_YEAST  303 ERNERRVELETELTSHNWSEERKSRQLSSLGKKESQFLRFLRLRRTRLSLEDFHIVKVIGKGAFGEVRLVQKKDTGKIYAMKS
21  DMK_HUMAN   33  EKGRQTEGGAFPLVSSALSGDPRF.FSPTTPPAEPIVVRLKEVRLQRDDFEILKVIGRGAESEVAVKMKQTGQVYAMKI
```

```
       Seq. ID No.:
 17    andcot       579 PRLTSNIDVSYFPIDEIPQEDTSAIHRAQARAMP.....DEQNAEMSLPFIGYTYKAFNAFQAS........
 18    COT1_NEUCR   557 PRLTSAIDTTYFPTDEIDQTDNATLLKAQQAARGAAAPAQQEESPELSLPFIGYTFKRFDNNFR........
 19    S70706       602 PRLTSAIDTTYFPTDEIDQTDNATVLKAQAIQQARSGIPQVEESPEMSLPFIGYTFKRFDNNFR........
 22    ORB6_SCHPO   409 PNLKSITDTHYFPVDELEQVPEQPVTQQPASVDPQTLEQT......NLAFIGYTYKKFNYLTMKGAL.....
 20    KNQ1_YEAST   689 PKLSSITDTRFFPTDELENVPDSPAMAQAAKQREQMTKQGGSAPVKEDIPFIGYTYSRFDYLTRKNAL....
 21    DMK_HUMAN    366 PDFEGATDTCNFDLVE......DGLTAMVSGGGETLSDIREGAPLGVHLPFVGYSYSCMALRDSEVPGTPMEVEAEQLL 21    DMK_HUMAN    440 EPHVQAPSLEPSVSPQDETAEVAVPAAEAEAEVTLRELQEALEEEVLTRQSLSREMEAIRTDNQNFASQLREAEAR 21    DMK_HUMAN    520 NRDLEAHVRQLQERMELLQAEGATAVTGVPSPRATDPPSHLDGPPAVAVGQCPLVGPMHRRHLLLPARVPRPGLSEAL

21    DMK_HUMAN    600 SLLLFAVVLSRAAALGCIGLVAHAGQLTAVWRRPGAARAP       639
```

FIG. 7C

| FIG. 7A |
| FIG. 7B |
| FIG. 7C |

FIG. 7

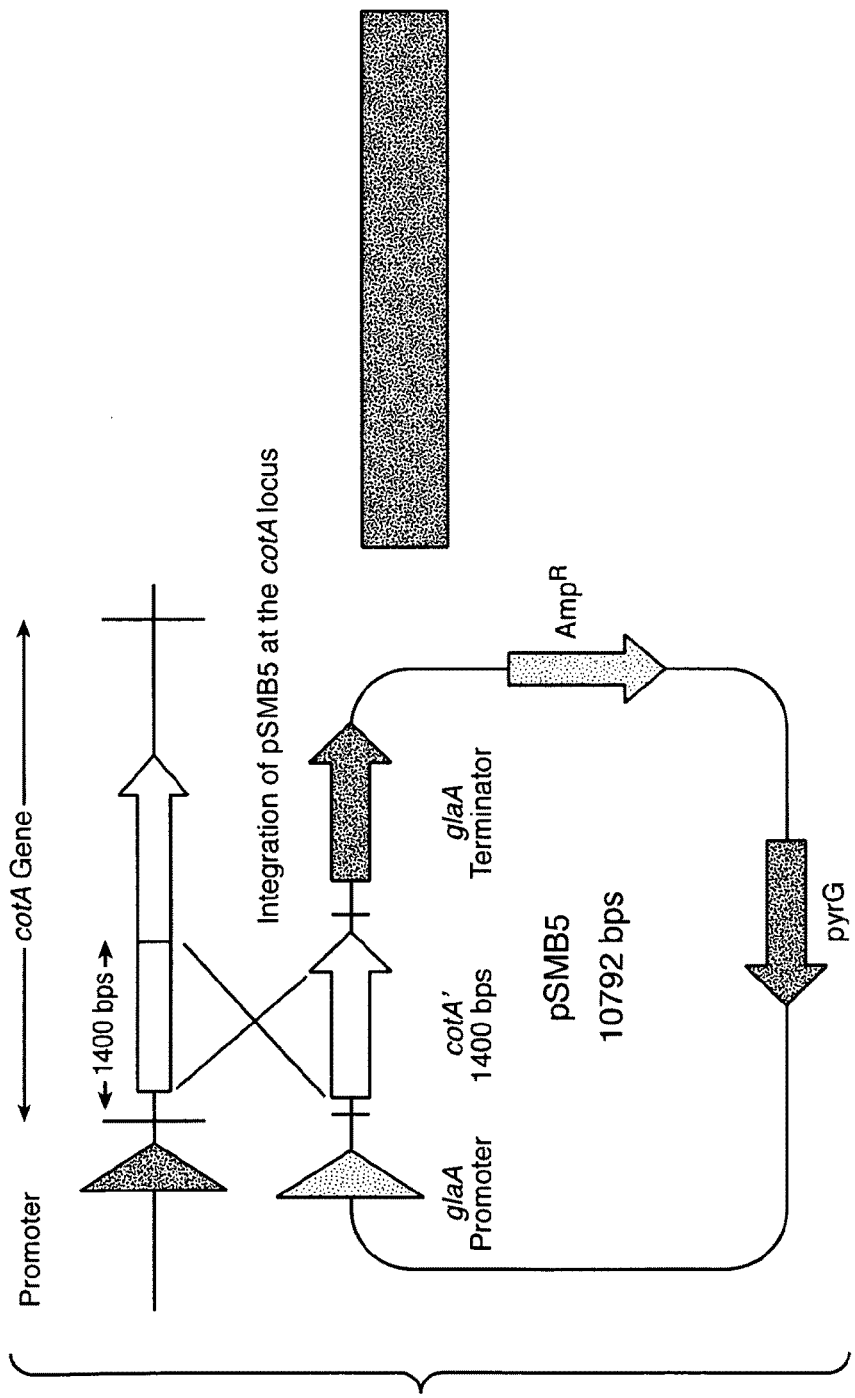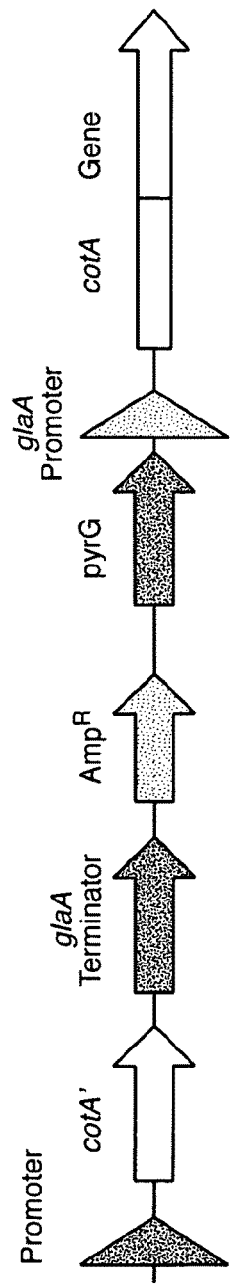
FIG. 8A
FIG. 8B

Wt Minimal Media
and 1% Maltose glaAp-cotA Minimal Media
and 1% Maltose

Wt Minimal Media
and 1% Xylose glaAp-cotA Minimal Media
and 1% Xylose

Wt YEPX (2% Xylose)

glaAp-cotA YEPX (2% Xylose)

Maltose

Xylose

```
ATGGATCCCA ACAACAACAA CCGACTCCAC CTGAATTTCG GGTACAATGA    50
TCGTGGTTTC AATGCGGCGG CGGCCAACAA CCGCGCCTAT CCCACTACCC   100
CCTCCGCCTT CCCCCAGCCG ATCTACCAAA ACCAGGGTCC CCAGGATTAC   150
ATGGACGCCC AGAACGGTGC CTACGCTCAA GGTGGTTATT TCATGGCCAA   200
TCCTTACCAA GCTCAGGCAG CCTACGGCCA GCCGCATTAT GGCCAGAACC   250
TGCAGTCCCC TCAGCCCGCC TACCAATCCC GCATGGGTTA CAGCGCGAAC   300
GATGGCACCA ACGGTTTGAT CCAGCAGTTC TCGAACCAGG ATCTGAATTC   350
CCCTCGCTCG GGTTTCTTTG CTCGTTCTGC CTCGCCAGCC CAGCGACTCC   400
GAACTGCCGG CTCCCCCGCC CCGGGCAGC AACAGCCAGG CCACCTGGCG   450
CCTCCTATGC CTCGTAGCCC TCGCACCCCC GCGGAGAACG AAGAGTTGCA   500
ACGGTACCCG GAACGTTACT CAGAGAATGT TCACAAGCGT GGCAAGGCAG   550
CCAAGGAGCT GGTCAGCGTC TTCTTCAATG AGAACATTGA GCGCGCACGC   600
GATCGCAACA TGCGGTGAGT ATTCCACACA ATGCCACGGC CTCCCTCCCA   650
ACCCAACAGG GAATTTGGTA TCGCTGACTC GGGTGCTTTT CATAGGTCTG   700
CTGAGCTGGA CAAGATGATC CGTGAACCCA GTATTCCCAA GGAGAACAAG   750
TGCAAGGACG CAGAGGTGCT TGCTAAGAAG GAATCGAATT CCTCCGGTT   800
CCTTCGCACC AAGGAGACCC CGCAGAACTT CCAGACCATC AAGATCATCG   850
GAAAGGGCGC GTTTGGTGAA GTGAAGCTGG TACAACGGAA GACCGATGGC   900
AAGATTTACG CACTGAAGTC GTTGATCAAA ACGGAGATGT TCAAGAAGGA   950
CCAGCTGGCT CACGTTCGCG CGGAACGTGA TATCCTTGCT GATTCCAAGG  1000
ACAACCCGTG GTTGGTGAAG CTGCATGCTT CTTTCCAGGA CACTGCCTAC  1050
TTGTATTTGC TGATGGAATT CTTGCCTGGT GGTGACTTGA TGACCATGTT  1100
GATCAAGTAC GAGATCTTCT CCGAGGATAT CACTCGGTTC TATATGGCCG  1150
AAATTGTCAT GGCGATCGAG GCTGTTCACA AGCTCGGCTT CCTTCACCGG  1200
TAAGTACTAG ATGCTCGATG CTGCCAGCAG ATGCAAAGTT GAAGTTTCAC  1250
GGGGCGGCAG GTGCTAATTG TTTTTGTCTA TAGTGATATC AAGCCTGATA  1300
ACATCCTTCT GGATCGCGGT GGTCACGTCA AGCTGACGGA CTTTGGTCTG  1350
TCCACGGGAG GAAAGAAGAC CCACGACAAC TCCTACTATC AGAATCTGCT  1400
GAAGAACTCG ACGTCAAAGG ACAAGAACCG CAACTCTGGT TACTTCAACG  1450
ATGCGATCAA CCTGACAGTC TCCAACCGTG GCCAGATCAA CACCTGGAGA  1500
AAGTCTCGTC GTGCAATGGC ATACTCGACG GTCGGAACTC CGGACTATAT  1550
CGCCCCCGAG ATCTTCAACG GCCAAGGATA CACCTACCTG TGCGATTGGT  1600
GGTCTGTAGG TGCTATCATG TTCGAGTGCC TTGTGGGTTG GCCCCCGTTC  1650
TGCGCGGAAG ACACCACCGA CACCTACCGC AAGATTGTGA ACTGGAGAGA  1700
ATGCTTGTAC TTCCCTGAGG AACTCACCCT TTCGCGCGAT CCGAGGGTC   1750
TCATCCGAAG GTAAGCTTTG TGCACATCAT ATGCTTATGT ATCATGCTAA  1800
CTCAGGATTA GCTTCCTCTG CGACGCAGAA CACCGTATCG GAAGCGATGG  1850
CGGCCAATTC GGCGGCGCAA CGCAGATCAA GAACCACCCC TTCTTCCGCG  1900
GCGTCGTTTG GGAGCAACTG CGCAGCATCC GCGCGCCGTT CGAACCAAGA  1950
CTGAGCTCGA ACATTGACGT GTCGTACTTC CCGATCGATG AGATTCCTCA  2000
GGAGGATACG AGTGCCATCC ACCGCGCTCA GGCTCGCGCC AAGCCGGACG  2050
AGCAGGAGGC GGAGATGAGC CTTCCATTCA TCGGATACAC CTACAAAGCG  2100
TTCAACGCCT TCCAGGGAAA TTGAAGATAC AGTCGA                 2136
```

Figure 11: Full-length cotA from A. niger (SEQ ID NO:13)

FIG. 11

```
CGGGATAGGG CTCGGAAAAG CGAGGGCTTC AGAGCATAAG AACATCATCA    50
GAAAGTGGAG CTTTCGTAGC ACAGTGTCGT GAGGTCCGTC TGATATGCC    100
CTGAAAAGTA AGCGTAGTGA GTGGGATGCT CTTCTCGCTT TTGAACATGA   150
CCGTGACTCT GTCTCAATCC ACACTCAATA CCTTTGTCTC CGTGATATGT   200
TTCAGATATA GAACCTTAAT GAAGAGCCAA CTTTATGACA AATGCATCTT   250
CGAGGGGTGG GTGTTGTATA GAGGCAGCGC GGGTGGGCCC CGCGGTCTTC   300
CGTAGCCCAA CTCCCAAAAC AGTCCAGGGT AACGTACTGG GCACCACCGC   350
ACTGCTTTTA AGCTACTGCT GGTCTTTAAG TCTGGACTCT CGATAACTTG   400
TTGCGGCTTT GCTTTTTCTT TGGTGCTTAT CAACCCAGGT GACTTTGCGA   450
CCACAGAATC GTTGTCGCTT GCTCAATCGC CTCCTGATCG ATTATCCCTC   500
TAAGGAGAGC TTGTCCAGTC GGGAGCGCTC AACACTCCA CTATAGTAAC    550
ACTGTTCCTT CCCCTCAAGC CGCACTCGCT CACTTGTCTC CTGAAGCCAC   600
CGCTTCTTCC CACTAACCTT CCCCTCCCCC CTTTACACTT GCACACCCCC   650
CCCTTATATC CATCACCTTC CTCCATTCCT CATCTCGCCG TCCGTCCAAT   700
TTTGGTAGTC TGGAGGGCAC TCTTCCAAAA TGGACCCCAA CAACAATCGC   750
CCCCACCTGA ACTTCGGCTA CAATGAACGT GCCTTCAACC CTGCGGCCGC   800
AAACAACCGC GCGTATCCCA CCACGCCCTC CGCATTTCCT CAGCCGATCT   850
ACCAGAGCCA GAGCCCCCAG GACTACATGG ACGCTCAGAA TGGTGTTTAT   900
GGTCAGGGAT ATTTCATGCC GAACAACTAC CCTGCGCAGG CTGCCTATGC   950
CCAGCCCCAT TACGGCCAAC CCAATCTCCA GTCTCCTCAG CCCGCCTATC  1000
AGTCTCGAAT GGGATACAAT GTCAGCCCCA ACGATGGAAC AAATGGTTTG  1050
ATACAGCAGT TCTCGAATCA GGATTAAAC TCGAACCGAA CGGGTTTCTT   1100
CAATCGCTCC GCTTCGCCTG CTCAAAGACC CCGTACTGCA GGCAATACAG  1150
CCCCCGGACA GCAGCAGCAA CCTGGACACT TGGCCCCTCC AGTGCCTCGC  1200
AGCCCTCGGC TGCCCCCCGA GAACGAAGAA CTTCAACGCT ACCCAGAGCG  1250
CTTCTCTGAA AATGTTCACA AACGTGGAAA AGCTGCGAAG GAGTTGGTCA  1300
ACGTATTCTT TCACGAGAAT ATCGAGCGTG CGCGTGATCG CAACATGCGG  1350
TGGGTTTTTG CTACTGAGCG CCGTATTTCT CTAAAAAGAA TTTTGCTAAC  1400
TGGAGTTATA ACTGTACAGT TCGGCGGAGC TCGACAAGAT GATGCGCGAC  1450
CCCAACATTT CACAAGATGC AAAGGTGAAG GAGGCGGAAA TGGTTGGAAA  1500
GAAAGAGTCG ACATTCCTTC GCTTCCTTCG GACACCAGAA ACTCCTGCCA  1550
ACTTCCAAAC CATCAAGATT ATTGGAAAGG GTGCTTTTGG TGAAGTTAAG  1600
CTGGTGCAGA GGAAGTCTGA TAACAAGATC TATGCGCTTA AGTCGCTGAT  1650
CAAATCAGAG ATGTTTAAGA AAGATCAGCT CGCCCACGTT CGTGCTGAAC  1700
GTGATATTCT AGCTGACTCG AAGGACAACC CTTGGCTTGT CAAGCTCCAT  1750
GCTTCATTCC AGGATCCCGC ATACCTATAC CTCCTGATGG AGTTCTTACC  1800
TGGAGGTGAT TTGATGACCA TGCTTATTAA GTACAAATA TTCTCTGAAG   1850
ATATCACACG CTTCTACATG GCGGAAATTG TGATGGCGAT TGAGGCGGTT  1900
CACAAGCTGG GTTTCCTTCA CCGGTGAGAA TAACAATCCT GGTCTCTCGT  1950
ACCATATACA GCGTGCTAAT ATACTTGTAC TATAGAGATA TTAAACCTGA  2000
CAACATCCTT CTCGATCGTG GCGGTCACGT CAAGCTGACC GATTTCGGTC  2050
TCTCAACTGG AGGCAAGAAA ACTCACGACA ACTCATACTA TCAGAACCTG  2100
TTGAAGAATT CAACATCCAA GGATAAGAAC CGAAACTCTG GATACTTCAA  2150
CGATGCTATC AACTTGACAG TATCGAACCG TGGGCAGATC AACACCTGGA  2200
GAAAATCTCG CAGGGCTATG GCTTACTCCA CTGTCGGAAC ACCTGACTAC  2250
ATTGCACCCG AAATTTTAA TGGTCAAGGA TACACCTATC TTTGCGACTG    2300
GTGGTCCGTC GGTGCCATCA TGTTTGAATG TCTCGTGGGC TGGCCTCCAT  2350
TCTGCGCCGA GGATACGACC GACACCTATC GCAAGATTGT GAACTGGAGG  2400
```

Figure 12:Full length *A. nidulans cotA* (Andcot)(SEQ ID NO:14)

FIG. 12A

```
GAATGCCTAT ATTTCCCCGA AGAATTGACA CTGTCTCGTG AATCGGAGGG  2450
TCTGATTCGA AGGTATGTTA TGTCAGCAAT CCATTTGAGC TGCTTGTCTA  2500
ACCGGAGATC AGCTTCCTAT GTGACGCAGA ACACCGCATC GGCAACGAAG  2550
GTGGCCAATA CGGAGGTGCT ACACAGATCA AAAATCACCC ATTCTTCCGC  2600
GGGGTAGTAT GGGATCAACT GCGCAAAATC CGGGCACCGT TCGAACCCAG  2650
ACTGACGTCA AATATCGACG TATCATATTT CCCGATTGAC GAGATTCCTC  2700
AGGAGGATAC CAGCGCCATT CACCGCGCCC AGGCACGTGC CATGCCGGAT  2750
GAGCAGAATG CTGAGATGAG CCTGCCTTTT ATCGGATACA CATACAAAGC  2800
ATTCAACGCC TTCCAGGCCA GTTGAGCATG CATTTAAAGT AAGAAATATA  2850
TTTGAATGAG CCGATGATGG ATGCCATTGG AAAGTTTTGA AGCGGGCGGG  2900
CTTGCGTTGA TAACTTTTCA ATGGCGCATC CAGGTTTTTG TGTCGGTCGG  2950
CATAGACCCT TGTTGATTGG TATTTTCATC AAGCATATAG CGCATACATC  3000
ATGTCACTGG ACACATGAGC ATCTCACTAC CATATGTG              3038
```

Figure 12: Full length A. nidulans cotA (Andcot)
(SEQ ID NO:14)(cont.)

FIG. 12B

```
GAATTCAGAT TGACATCAAG CCTGATAACA TCCTTCTGGA TCGCGGTGGT   50
CACGTCAAGC TGACGGACTT TGGTCTGTCC ACGGGAGGAA AGAAGACCCA  100
CGACAACTCC TACTATCAGA ATCTGCTGAA GAACTCGACG TCAAAGGACA  150
AGAACCGCAA CTCTGGTTAC TTCAACGATG CGATCAACCT GACAGTCTCC  200
AACCGTGGCC AGATCAACAC CTGGAGAAAG TCTCGTCGTG CAATGGCATA  250
CTCGACGGTA GGCATCCGG                                    269
```

Figure 13:269 bp probe from A. niger (SEQ ID NO:15)

FIG. 13

Figure 14: Protein sequence encoded by A. niger cotA without introns

SEQUENCE LISTING

<160> NUMBER OF SEQ ID NOS: 23

<210> SEQ ID NO 1
<211> LENGTH: 1784
<212> TYPE: DNA

<213> ORGANISM: Aspergillus niger

<400> SEQUENCE: 1

```
tttccatcat ggatcccaac aacaacaacc gactccacct gaatttcggg tacaatgatc    60
gtggtttcaa tgcggcggcg gccaacaacc gcgcctatcc cactaccccc tccgccttcc   120
cccagccgat ctaccaaaac cagggtcccc aggattacat ggacgcccag aacggtgcct   180
acgctcaagg tggttatttc atggccaatc cttaccaagc tcaggcagcc tacggccagc   240
cgcattatgg ccagaacctg cagtcccctc agcccgccta cccatcccgc atgggttaca   300
gcgcgaacga tggcaccaac ggtttgatcc agcagttctc gaaccaggat ctgaattccc   360
ctcgctcggg tttctttgct cgttctgcct cgccagccca gcgaccccga actgccggct   420
cccccgcccc cgggcagcaa cagccaggcc acctggcgcc tcctatgcct cgtagccctc   480
gcaccccgc ggagaacgaa gagttgcaac ggtacccgga acgttactca gagaatgttc   540
acaagcgtgg caaggcagcc aaggagctgg tcagcgtctt cttaatgaga caatgagcg   600
cgcacgcgat cgcaacatgc ggtgagtatt ccacacaatg ccacggcctc cctcccaacc   660
caacagggaa tttggtatcg ctgactcggg tgcttttcat aggtctgctg agctggacaa   720
gatgatccgt gaacccagta ttcccaagga gaacaagtgc aaggacgcag aggtgcttgc   780
taagaaggaa tcgaatttcc tccggttcct tcgcaccaag gagaccccgc agaacttcca   840
gaccatcaag atcatcggaa agggcgcgtt tggtgaagtg aagctggtac aacggaaggc   900
cgatggcaag atttacgcac tgaagtcgtt gatcaaaacg gagatgttca gcaaggacc   960
agctgctcac gttcgcgcgg aacgtgatat ccttgctgat ccaaggaca acccgtggtt  1020
ggtgaagctg catgcttctt ccaggacac tgcctacttg tatttgctga tggaattctt  1080
gcctggtggt gacttgatga ccatgttgat caagtacgag atcttctccg aggatatcac  1140
tcggttctat atggccgaaa ttgtcatggc gatcgaggct gttcacaagc tcggcttcct  1200
tcaccgggac atcaagcctg ataacatcct tctggatcgc ggtggtcacg tcaagctgac  1260
ggactttggt ctgtccacgg gaggaaagaa gacccacgac aactcctact atcagaatct  1320
gctgaagaac tcgacgtcaa aggacaagaa ccgcaactct ggttacttca cgatgcgat  1380
caacctgaca gtctccaacc gtggccagat caacacctgg agaaagtctc gtcgtgcaat  1440
ggcatactcg acggtcggaa ctccggacta tatcgccccc gagatcttca cggccaagg  1500
atacacctac ctgtgcgatt ggtggtctgt aggtgctatc atgttcgagt gccttgtggg  1560
ttggccccg ttctgcgcgg aagacaccac cgacacctac cgcaagattg tgaactggag  1620
agaatgcttg tacttccctg aggaactcac cctttcgcgc gattccgagg gtctcatccg  1680
aaggtaagct tgaagccgag aagcgtgagg ccagaaaggc cgcaagcacg aagaacattg  1740
acggagaagt gaagaaggaa gactctgacc cactaggcaa ccag                   1784
```

<210> SEQ ID NO 2
<211> LENGTH: 250
<212> TYPE: PRT
<213> ORGANISM: Aspergillus niger

<400> SEQUENCE: 2

```
Met Glu Pro Asn Asn Asn Asn Arg Leu His Leu Asn Phe Gly Tyr Asn
  1               5                  10                  15

Asp Arg Gly Phe Asn Ala Ala Ala Ala Asn Asn Arg Ala Tyr Pro Thr
             20                  25                  30

Thr Pro Ser Ala Phe Pro Gln Pro Ile Tyr Gln Asn Gln Gly Pro Gln
```

```
                    35                  40                  45
Asp Tyr Met Asp Ala Gln Asn Gly Ala Tyr Ala Gln Gly Gly Tyr Phe
 50                  55                  60

Met Ala Asn Pro Tyr Gln Ala Gln Ala Ala Tyr Gly Gln Pro His Tyr
 65                  70                  75                  80

Gly Gln Asn Leu Gln Ser Pro Gln Pro Ala Tyr Pro Ser Arg Met Gly
                 85                  90                  95

Tyr Ser Ala Asn Asp Gly Thr Asn Gly Leu Ile Gln Gln Phe Ser Asn
                100                 105                 110

Gln Asp Leu Asn Ser Pro Arg Ser Gly Phe Phe Ala Arg Ser Ala Ser
                115                 120                 125

Pro Ala Gln Arg Pro Arg Thr Ala Gly Ser Pro Ala Pro Gly Gln Gln
130                 135                 140

Gln Pro Gly His Leu Ala Pro Pro Met Pro Arg Ser Pro Arg Thr Pro
145                 150                 155                 160

Ala Glu Asn Glu Glu Leu Gln Arg Tyr Pro Glu Arg Tyr Ser Glu Asn
                165                 170                 175

Val His Lys Arg Gly Lys Ala Ala Lys Glu Leu Val Ser Val Phe Phe
                180                 185                 190

Asn Glu Asn Asn Glu Arg Ala Arg Asp Arg Asn Met Arg Ser Ala Glu
                195                 200                 205

Leu Asp Lys Met Ile Arg Glu Pro Ser Ile Pro Lys Glu Asn Lys Cys
                210                 215                 220

Lys Asp Ala Glu Val Leu Ala Lys Lys Glu Ser Asn Phe Leu Arg Phe
225                 230                 235                 240

Leu Arg Thr Lys Glu Thr Pro Gln Asn Phe
                245                 250

<210> SEQ ID NO 3
<211> LENGTH: 3038
<212> TYPE: DNA
<213> ORGANISM: Aspergillus nidulans

<400> SEQUENCE: 3
cgggataggg ctcggaaaag cgagggcttc agagcataag aacatcatca gaaagtggag     60
ctttcgtagc acagtgtcgt gaggtccgtc tgatatggcc ctgaaaagta agcgtagtga    120
gtgggatgct cttctcgctt ttgaacatga ccgtgactct gtctcaatcc acactcaata    180
cctttgtctc cgtgatatgt ttcagatata gaaccttaat gaagagccaa ctttatgaca    240
aatgcatctt cgagggggtgg gtgttgtata gaggcagcgc gggtgggccc cgcggtcttc    300
cgtagcccaa ctcccaaaac agtccagggt aacgtactgg gcaccaccgc actgctttta    360
agctactgct ggtctttaag tctggactct cgataacttg ttgcggcttt gcttttttctt    420 tggtgcttat caacccaggt gactttgcga ccacagaatc gttgtcgctt gctcaatcgc    480
ctcctgatcg attatccctc taaggagagc ttgtccagtc gggagcgctc caacactcca    540
ctatagtaac actgttcctt ccctcaagc cgcactcgct cacttgtctc ctgaagccac    600
cgcttcttcc cactaacctt cccctccccc ctttacactt gcacaccccc cccttatatc    660
catcaccttc ctccattcct catctcgccg tccgtccaat tttggtagtc tggagggcac    720
tcttccaaaa tggaccccaa caacaatcgc ccccacctga acttcggcta caatgaacgt    780
gccttcaacc ctgcggccgc aaacaaccgc gcgtatccca ccacgccctc cgcatttcct    840
cagccgatct accagagcca gagccccag gactacatgg acgctcagaa tggtgtttat    900
```

-continued

```
ggtcagggat atttcatgcc gaacaactac cctgcgcagg ctgcctatgc ccagccccat    960
tacggccaac ccaatctcca gtctcctcag cccgcctatc agtctcgaat gggatacaat   1020
gtcagcccca acgatggaac aaatggtttg atacagcagt tctcgaatca ggatttaaac   1080
tcgaaccgaa cgggtttctt caatcgctcc gcttcgcctg ctcaaagacc ccgtactgca   1140
ggcaatacag cccccggaca gcagcagcaa cctggacact tggcccctcc agtgcctcgc   1200
agccctcggc tgcccccccga gaacgaagaa cttcaacgct acccagagcg cttctctgaa   1260
aatgttcaca acgtggaaa agctgcgaag gagttggtca acgtattctt tcacgagaat    1320
atcgagcgtg cgcgtgatcg caacatgcgg tgggttttttg ctactgagcg ccgtatttct   1380
ctaaaaagaa ttttgctaac tggagttata actgtacagt tcggcggagc tcgacaagat   1440
gatgcgcgac cccaacattt cacaagatgc aaggtgaag gaggcggaaa tggttggaaa    1500
gaaagagtcg acattccttc gcttccttcg gacaccagaa actcctgcca acttccaaac   1560
catcaagatt attggaaagg gtgcttttgg tgaagttaag ctggtgcaga ggaagtctga    1620
taacaagatc tatgcgctta agtcgctgat caaatcagag atgtttaaga agatcagct    1680
cgcccacgtt cgtgctgaac gtgatattct agctgactcg aaggacaacc cttggcttgt    1740
caagctccat gcttcattcc aggatcccgc ataccttatc ctcctgatgg agttcttacc    1800
tggaggtgat tgatgacca tgcttattaa gtacgaaata ttctctgaag atatcacacg     1860
cttctacatg gcggaaattg tgatggcgat tgaggcggtt cacaagctgg gtttccttca   1920
ccggtgagaa taacaatcct ggtctctcgt accatataca gcgtgctaat atacttgtac   1980
tatagagata ttaaacctga caacatcctt ctcgatcgtg gcggtcacgt caagctgacc    2040
gatttcggtc tctcaactgg aggcaagaaa actcacgaca actcatacta tcagaacctg    2100
ttgaagaatt caacatccaa ggataagaac cgaaactctg gatacttcaa cgatgctatc    2160
aacttgacag tatcgaaccg tgggcagatc aacacctgga gaaaatctcg cagggctatg    2220
gcttactcca ctgtcggaac acctgactac attgcacccg aaatttttaa tggtcaagga    2280
tacacctatc tttgcgactg gtggtccgtc ggtgccatca tgtttgaatg tctcgtgggc    2340
tggcctccat tctgcgccga ggatacgacc gacacctatc gcaagattgt gaactggagg    2400
gaatgcctat atttccccga gaattgaca ctgtctcgtg aatcggaggg tctgattcga     2460
aggtatgtta tgtcagcaat ccatttgagc tgcttgtcta accggagatc agcttcctat    2520
gtgacgcaga acaccgcatc ggcaacgaag gtggccaata cggaggtgct acacagatca    2580
aaaatcaccc attcttccgc ggggtagtat gggatcaact gcgcaaaatc cgggcaccgt    2640
tcgaacccag actgacgtca aatatcgacg tatcatattt cccgattgac gagattcctc    2700
aggaggatac cagcgccatt caccgcgccc aggcacgtgc catgccggat gagcagaatg    2760
ctgagatgag cctgccttt atcggataca catacaaagc attcaacgcc ttccaggcca     2820
gttgagcatg catttaaagt aagaaatata tttgaatgag ccgatgatgg atgccattgg    2880
aaagttttga agcgggcggg cttgcgttga taacttttca atggcgcatc caggtttttg    2940
tgtcggtcgg catagaccct tgttgattgg tattttcatc aagcatatag cgcatacatc    3000
atgtcactgg acacatgagc atctcactac catatgtg                            3038
```

<210> SEQ ID NO 4
<211> LENGTH: 637
<212> TYPE: PRT
<213> ORGANISM: Aspergillus nidulans

<400> SEQUENCE: 4

```
Met Asp Pro Asn Asn Arg Pro His Leu Asn Phe Gly Tyr Asn Glu
 1               5                  10                  15

Arg Ala Phe Asn Pro Ala Ala Asn Asn Arg Ala Tyr Pro Thr Thr
                20                  25                  30

Pro Ser Ala Phe Pro Gln Pro Ile Tyr Gln Ser Gln Ser Pro Gln Asp
             35                  40                  45

Tyr Met Asp Ala Gln Asn Gly Val Tyr Gly Gln Gly Tyr Phe Met Pro
 50                  55                  60

Asn Asn Tyr Pro Ala Gln Ala Ala Tyr Ala Gln Pro His Tyr Gly Gln
 65                  70                  75                  80

Pro Asn Leu Gln Ser Pro Gln Pro Ala Tyr Gln Ser Arg Met Gly Tyr
                 85                  90                  95

Asn Val Ser Pro Asn Asp Gly Thr Asn Gly Leu Ile Gln Gln Phe Ser
                100                 105                 110

Asn Gln Asp Leu Asn Ser Asn Arg Thr Gly Phe Phe Asn Arg Ser Ala
                115                 120                 125

Ser Pro Ala Gln Arg Pro Arg Thr Ala Gly Asn Thr Ala Pro Gly Gln
 130                 135                 140

Gln Gln Gln Pro Gly His Leu Ala Pro Pro Val Pro Arg Ser Pro Arg
145                 150                 155                 160

Leu Pro Pro Glu Asn Glu Glu Leu Gln Arg Tyr Pro Glu Arg Phe Ser
                165                 170                 175

Glu Asn Val His Lys Arg Gly Lys Ala Ala Lys Glu Leu Val Asn Val
                180                 185                 190

Phe Phe His Glu Asn Ile Glu Arg Ala Arg Asp Arg Asn Met Arg Ser
                195                 200                 205

Ala Glu Leu Asp Lys Met Met Arg Asp Pro Asn Ile Ser Gln Asp Ala
 210                 215                 220

Lys Val Lys Glu Ala Glu Met Val Gly Lys Lys Glu Ser Thr Phe Leu
225                 230                 235                 240

Arg Phe Leu Arg Thr Pro Glu Thr Pro Ala Asn Phe Gln Thr Ile Lys
                245                 250                 255

Ile Ile Gly Lys Gly Ala Phe Gly Glu Val Lys Leu Val Gln Arg Lys
                260                 265                 270

Ser Asp Asn Lys Ile Tyr Ala Leu Lys Ser Leu Ile Lys Ser Glu Met
                275                 280                 285

Phe Lys Lys Asp Gln Leu Ala His Val Arg Ala Glu Arg Asp Ile Leu
                290                 295                 300

Ala Asp Ser Lys Asp Asn Pro Trp Leu Val Lys Leu His Ala Ser Phe
305                 310                 315                 320

Gln Asp Pro Ala Tyr Leu Tyr Leu Leu Met Glu Phe Leu Pro Gly Gly
                325                 330                 335

Asp Leu Met Thr Met Leu Ile Lys Tyr Glu Ile Phe Ser Glu Asp Ile
                340                 345                 350

Thr Arg Phe Tyr Met Ala Glu Ile Val Met Ala Ile Glu Ala Val His
                355                 360                 365

Lys Leu Gly Phe Leu His Arg Asp Ile Lys Pro Asp Asn Ile Leu Leu
                370                 375                 380

Asp Arg Gly Gly His Val Lys Leu Thr Asp Phe Gly Leu Ser Thr Gly
385                 390                 395                 400

Gly Lys Lys Thr His Asp Asn Ser Tyr Tyr Gln Asn Leu Leu Lys Asn
                405                 410                 415
```

```
Ser Thr Ser Lys Asp Lys Asn Arg Asn Ser Gly Tyr Phe Asn Asp Ala
            420                 425                 430

Ile Asn Leu Thr Val Ser Asn Arg Gly Gln Ile Asn Thr Trp Arg Lys
        435                 440                 445

Ser Arg Arg Ala Met Ala Tyr Ser Thr Val Gly Thr Pro Asp Tyr Ile
450                 455                 460

Ala Pro Glu Ile Phe Asn Gly Gln Gly Tyr Thr Tyr Leu Cys Asp Trp
465                 470                 475                 480

Trp Ser Val Gly Ala Ile Met Phe Glu Cys Leu Val Gly Trp Pro Pro
                485                 490                 495

Phe Cys Ala Glu Asp Thr Thr Asp Thr Tyr Arg Lys Ile Val Asn Trp
            500                 505                 510

Arg Glu Cys Leu Tyr Phe Pro Glu Glu Leu Thr Leu Ser Arg Glu Ser
        515                 520                 525

Glu Gly Leu Ile Arg Ser Phe Leu Cys Asp Ala Glu His Arg Ile Gly
    530                 535                 540

Asn Glu Gly Gly Gln Tyr Gly Gly Ala Thr Gln Ile Lys Asn His Pro
545                 550                 555                 560

Phe Phe Arg Gly Val Val Trp Asp Gln Leu Arg Lys Ile Arg Ala Pro
                565                 570                 575

Phe Glu Pro Arg Leu Thr Ser Asn Ile Asp Val Ser Tyr Phe Pro Ile
            580                 585                 590

Asp Glu Ile Pro Gln Glu Asp Thr Ser Ala Ile His Arg Ala Gln Ala
        595                 600                 605

Arg Ala Met Pro Asp Glu Gln Asn Ala Glu Met Ser Leu Pro Phe Ile
    610                 615                 620

Gly Tyr Thr Tyr Lys Ala Phe Asn Ala Phe Gln Ala Ser
625                 630                 635

<210> SEQ ID NO 5
<211> LENGTH: 264
<212> TYPE: DNA
<213> ORGANISM: Trichoderma reesei
<220> FEATURE:
<221> NAME/KEY: misc_feature
<222> LOCATION: (1)...(264)
<223> OTHER INFORMATION: n = A,T,C or G

<400> SEQUENCE: 5
ctgctggacc gtggcggccc cgtcaagctg accgactttg gtctctccac gggcttccac      60
cgtctgcacg acaacaacta ctaccagcag ctgctgcagg gccgctccaa ccgcccgcgt     120
gaccgcacct cggttgccat tgatcagatt aacctcacag tcagcaaccg atctcagatt     180
aacgactgga gacgatctcg acggctgatg gcttactcca ccgtcggtac accagactac     240
atcgccccng aaattctcta cctc                                            264

<210> SEQ ID NO 6
<211> LENGTH: 88
<212> TYPE: PRT
<213> ORGANISM: Trichoderma reesei

<400> SEQUENCE: 6

Leu Leu Asp Arg Gly Gly Pro Val Lys Leu Thr Asp Phe Gly Leu Ser
1               5                   10                  15

Thr Gly Phe His Arg Leu His Asp Asn Asn Tyr Tyr Gln Gln Leu Leu
            20                  25                  30

Gln Gly Arg Ser Asn Arg Pro Arg Asp Arg Thr Ser Val Ala Ile Asp
```

```
                35                  40                  45
Gln Ile Asn Leu Thr Val Ser Asn Arg Ser Gln Ile Asn Asp Trp Arg
    50                  55                  60

Arg Ser Arg Arg Leu Met Ala Tyr Ser Thr Val Gly Thr Pro Asp Tyr
65                  70                  75                  80

Ile Ala Pro Glu Ile Leu Tyr Leu
                85

<210> SEQ ID NO 7
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G

<400> SEQUENCE: 7
gayatyaarc cngayaa                                                  17

<210> SEQ ID NO 8
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G

<400> SEQUENCE: 8
tcnggngcda trtartc                                                  17

<210> SEQ ID NO 9
<211> LENGTH: 17
<212> TYPE: DNA
<213> ORGANISM: Artificial Sequence
<220> FEATURE:
<223> OTHER INFORMATION: primer

<400> SEQUENCE: 9
acgtcgagtt cttcagc                                                  17

<210> SEQ ID NO 10
<211> LENGTH: 17
<212> TYPE: DNA
<213> ORGANISM: Artificial Sequence
<220> FEATURE:
<223> OTHER INFORMATION: primer

<400> SEQUENCE: 10
gcgatcaacc tgacagt                                                  17

<210> SEQ ID NO 11
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G
```

```
<400> SEQUENCE: 11
gayatyaarc cngamaa                                                      17

<210> SEQ ID NO 12
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(17)
<223> OTHER INFORMATION: n = A,T,C or G

<400> SEQUENCE: 12
tcnggngcka trtartc                                                      17

<210> SEQ ID NO 13
<211> LENGTH: 2136
<212> TYPE: DNA
<213> ORGANISM: Aspergillus niger

<400> SEQUENCE: 13
atggatccca acaacaacaa ccgactccac ctgaatttcg ggtacaatga tcgtggtttc         60 aatgcgcgg cggccaacaa ccgcgcctat cccactaccc cctccgcctt cccccagccg        120
atctaccaaa accagggtcc ccaggattac atggacgccc agaacggtgc ctacgctcaa       180
ggtggttatt tcatggccaa tccttaccaa gctcaggcag cctacggcca gccgcattat       240
ggccagaacc tgcagtcccc tcagcccgcc taccaatccc gcatgggtta cagcgcgaac       300
gatggcacca acggtttgat ccagcagttc tcgaaccagg atctgaattc ccctcgctcg       360
ggtttctttg ctcgttctgc ctcgccagcc cagcgactcc gaactgccgg ctccccccgcc      420 cccgggcagc aacagccagg ccacctggcg cctcctatgc ctcgtagccc ctcgcacccc      480
gcggagaacg aagagttgca acggtacccg gaacgttact cagagaatgt tcacaagcgt       540
ggcaaggcag ccaaggagct ggtcagcgtc ttcttcaatg agaacattga gcgcgcacgc       600
gatcgcaaca tgcggtgagt attccacaca atgccacggc ctccctccca acccaacagg       660
gaatttggta tcgctgactc gggtgctttt cataggtctg ctgagctgga caagatgatc       720
cgtgaaccca gtattcccaa ggagaacaag tgcaaggacg cagaggtgct tgctaagaag       780
gaatcgaatt tcctccggtt ccttcgcacc aaggagaccc gcagaacttc cagaccatc       840 aagatcatcg gaaagggcgc gtttggtgaa gtgaagctgg tacaacggaa gaccgatggc       900
aagatttacg cactgaagtc gttgatcaaa acggagatgt tcaagaagga ccagctggct       960
cacgttcgcg cggaacgtga tatccttgct gattccaagg acaacccgtg gttggtgaag      1020
ctgcatgctt cttttccagga cactgcctac ttgtatttgc tgatggaatt cttgcctggt      1080
ggtgacttga tgaccatgtt gatcaagtac gagatcttct ccgaggatat cactcggttc       1140
tatatggccg aaattgtcat ggcgatcgag ctgttcaca agctcggctt ccttcaccgg       1200
taagtactag atgctcgatg ctgccagcag atgcaaagtt gaagtttcac ggggcggcag      1260
gtgctaattg tttttgtcta tagtgatatc aagcctgata acatccttct ggatcgcggt      1320
ggtcacgtca agctgacgga ctttggtctg tccacgggag aaagaagac ccacgacaac       1380 tcctactatc agaatctgct gaagaactcg acgtcaaagg acaagaaccg caactctggt      1440
tacttcaacg atgcgatcaa cctgacagtc tccaaccgtg gccagatcaa cacctggaga      1500
aagtctcgtc gtgcaatggc atactcgacg gtcggaactc cggactatat cgcccccgag      1560
```

-continued

```
atcttcaacg gccaaggata cacctacctg tgcgattggt ggtctgtagg tgctatcatg   1620
ttcgagtgcc ttgtgggttg gccccccgttc tgcgcggaag acaccaccga cacctaccgc   1680
aagattgtga actggagaga atgcttgtac ttccctgagg aactcaccct ttcgcgcgat   1740
tccgagggtc tcatccgaag gtaagctttg tgcacatcat atgcttatgt atcatgctaa   1800
ctcaggatta gcttcctctg cgacgcagaa caccgtatcg gaagcgatgg cggccaattc   1860
ggcggcgcaa cgcagatcaa gaaccacccc ttcttccgcg gcgtcgtttg ggagcaactg   1920
cgcagcatcc gcgcgccgtt cgaaccaaga ctgagctcga acattgacgt gtcgtacttc   1980
ccgatcgatg agattcctca ggaggatacg agtgccatcc accgcgctca ggctcgcgcc   2040
aagccggacg agcaggaggc ggagatgagc cttccattca tcggatacac ctacaaagcg   2100
ttcaacgcct tccagggaaa ttgaagatac agtcga                           2136
```

<210> SEQ ID NO 14
<211> LENGTH: 3038
<212> TYPE: DNA
<213> ORGANISM: Aspergillus nidulans

<400> SEQUENCE: 14

```
cgggataggg ctcggaaaag cgagggcttc agagcataag aacatcatca gaaagtggag     60
ctttcgtagc acagtgtcgt gaggtccgtc tgatatggcc ctgaaaagta agcgtagtga    120
gtgggatgct cttctcgctt ttgaacatga ccgtgactct gtctcaatcc acactcaata    180
cctttgtctc cgtgatatgt ttcagatata gaaccttaat gaagagccaa ctttatgaca    240
aatgcatctt cgaggggtgg gtgttgtata gaggcagcgc gggtgggccc cgcggtcttc    300
cgtagcccaa ctcccaaaac agtccagggt aacgtactgg gcaccaccgc actgctttta    360
agctactgct ggtctttaag tctggactct cgataacttg ttgcggcttt gctttttctt    420
tggtgcttat caacccaggt gactttgcga ccacagaatc gttgtcgctt gctcaatcgc    480
ctcctgatcg attatccctc taaggagagc ttgtccagtc gggagcgctc caacactcca    540
ctatagtaac actgttcctt cccctcaagc cgcactcgct cacttgtctc ctgaagccac    600
cgcttcttcc cactaacctt cccctccccc ctttacactt gcacaccccc cccttatatc    660
catcaccttc ctccattcct catctcgccg tccgtccaat tttggtagtc tggagggcac    720
tcttccaaaa tggaccccaa caacaatcgc ccccacctga acttcggcta caatgaacgt    780
gccttcaacc ctgcggccgc aaacaaccgc gcgtatccca ccacgccctc cgcatttcct    840
cagccgatct accagagcca gagcccccag gactacatgg acgctcagaa tggtgtttat    900
ggtcagggat atttcatgcc gaacaactac cctgcgcagg ctgcctatgc ccagccccat    960
tacggccaac ccaatctcca gtctcctcag cccgcctatc agtctcgaat gggatacaat   1020
gtcagcccca acgatggaac aaatggtttg atacagcagt tctcgaatca ggatttaaac   1080
tcgaaccgaa cgggtttctt caatcgctcc gcttcgcctg ctcaaagacc ccgtactgca   1140
ggcaatacag cccccggaca gcagcagcaa cctggacact tggcccctcc agtgcctcgc   1200
agccctcggc tgccccccga gaacgaagaa cttcaacgct acccagagcg cttctctgaa   1260
aatgttcaca aacgtggaaa agctgcgaag gagttggtca acgtattctt tcacgagaat   1320
atcgagcgtg cgcgtgatcg caacatgcgg tgggtttttg ctactgagcg ccgtatttct   1380
ctaaaaagaa ttttgctaac tggagttata actgtacagt tcggcggagc tcgacaagat   1440
gatgcgcgac cccaacattt cacaagatgc aaaggtgaag gaggcggaaa tggttggaaa   1500
```

```
gaaagagtcg acattccttc gcttccttcg gacaccagaa actcctgcca acttccaaac    1560
catcaagatt attggaaagg gtgctttttgg tgaagttaag ctggtgcaga ggaagtctga    1620
taacaagatc tatgcgctta agtcgctgat caaatcagag atgtttaaga agatcagct     1680 cgcccacgtt cgtgctgaac gtgatattct agctgactcg aaggacaacc cttggcttgt    1740
caagctccat gcttcattcc aggatcccgc atacctatac ctcctgatgg agttcttacc    1800
tggaggtgat tgatgacca tgcttattaa gtacgaaata ttctctgaag atatcacacg     1860
cttctacatg gcggaaattg tgatggcgat tgaggcggtt cacaagctgg gtttccttca    1920
ccggtgagaa taacaatcct ggtctctcgt accatataca gcgtgctaat atacttgtac    1980
tatagagata ttaaacctga caacatcctt ctcgatcgtg gcggtcacgt caagctgacc    2040
gatttcggtc tctcaactgg aggcaagaaa actcacgaca actcatacta tcagaacctg    2100
ttgaagaatt caacatccaa ggataagaac cgaaactctg atacttcaa cgatgctatc     2160 aacttgacag tatcgaaccg tgggcagatc aacacctgga gaaaatctcg cagggctatg    2220
gcttactcca ctgtcggaac acctgactac attgcacccg aaatttttaa tggtcaagga    2280
tacacctatc tttgcgactg gtggtccgtc ggtgccatca tgtttgaatg tctcgtgggc    2340
tggcctccat tctgcgccga ggatacgacc gacacctatc gcaagattgt gaactggagg    2400
gaatgcctat atttccccga gaattgaca ctgtctcgtg aatcggaggg tctgattcga     2460
aggtatgtta tgtcagcaat ccatttgagc tgcttgtcta accggagatc agcttcctat    2520
gtgacgcaga acaccgcatc ggcaacgaag gtggccaata cggaggtgct acacagatca    2580
aaaatcaccc attcttccgc ggggtagtat gggatcaact gcgcaaaatc cgggcaccgt    2640
tcgaacccag actgacgtca aatatcgacg tatcatattt cccgattgac gagattcctc    2700
aggaggatac cagcgccatt caccgcgccc aggcacgtgc catgccggat gagcagaatg    2760
ctgagatgag cctgcctttt atcggataca catacaaagc attcaacgcc ttccaggcca    2820
gttgagcatg catttaaagt aagaaatata tttgaatgag ccgatgatgg atgccattgg    2880
aaagttttga agcgggcggg cttgcgttga aacttttca atggcgcatc caggttttttg    2940 tgtcggtcgg catagaccct tgttgattgg tattttcatc aagcatatag cgcatacatc    3000
atgtcactgg acacatgagc atctcactac catatgtg                            3038
```

<210> SEQ ID NO 15
<211> LENGTH: 269
<212> TYPE: DNA
<213> ORGANISM: Aspergillus niger

<400> SEQUENCE: 15

```
gaattcagat tgacatcaag cctgataaca tccttctgga tcgcggtggt cacgtcaagc      60
tgacggactt tggtctgtcc acgggaggaa agaagaccca cgacaactcc tactatcaga    120
atctgctgaa gaactcgacg tcaaaggaca agaaccgcaa ctctggttac ttcaacgatg    180 cgatcaaccct gacagtctcc aaccgtggcc agatcaacac ctggagaaag tctcgtcgtg    240
caatggcata ctcgacggta ggcatccgg                                       269
```

<210> SEQ ID NO 16
<211> LENGTH: 635
<212> TYPE: PRT
<213> ORGANISM: Aspergillus niger

<400> SEQUENCE: 16

Met Asp Pro Asn Asn Asn Asn Arg Leu His Leu Asn Phe Gly Tyr Asn

```
       1               5                  10                 15
Asp Arg Gly Phe Asn Ala Ala Ala Asn Asn Arg Ala Tyr Pro Thr
                20                  25                  30

Thr Pro Ser Ala Phe Pro Gln Pro Ile Tyr Gln Asn Gln Gly Pro Gln
                35                  40                  45

Asp Tyr Met Asp Ala Gln Asn Gly Ala Tyr Ala Gln Gly Gly Tyr Phe
                50                  55                  60

Met Ala Asn Pro Tyr Gln Ala Gln Ala Ala Tyr Gly Gln Pro His Tyr
65                  70                  75                  80

Gly Gln Asn Leu Gln Ser Pro Gln Pro Ala Tyr Gln Ser Arg Met Gly
                85                  90                  95

Tyr Ser Ala Asn Asp Gly Thr Asn Gly Leu Ile Gln Gln Phe Ser Asn
                100                 105                 110

Gln Asp Leu Asn Ser Pro Arg Ser Gly Phe Phe Ala Arg Ser Ala Ser
                115                 120                 125

Pro Ala Gln Arg Leu Arg Thr Ala Gly Ser Pro Ala Pro Gly Gln Gln
                130                 135                 140

Gln Pro Gly His Leu Ala Pro Pro Met Pro Arg Ser Pro Arg Thr Pro
145                 150                 155                 160

Ala Glu Asn Glu Glu Leu Gln Arg Tyr Pro Glu Arg Tyr Ser Glu Asn
                165                 170                 175

Val His Lys Arg Gly Lys Ala Ala Lys Glu Leu Val Ser Val Phe Phe
                180                 185                 190

Asn Glu Asn Ile Glu Arg Ala Arg Asp Arg Asn Met Arg Ser Ala Glu
                195                 200                 205

Leu Asp Lys Met Ile Arg Glu Pro Ser Ile Pro Lys Glu Asn Lys Cys
                210                 215                 220

Lys Asp Ala Glu Val Leu Ala Lys Lys Glu Ser Asn Phe Leu Arg Phe
225                 230                 235                 240

Leu Arg Thr Lys Glu Thr Pro Gln Asn Phe Gln Thr Ile Lys Ile Ile
                245                 250                 255

Gly Lys Gly Ala Phe Gly Glu Val Lys Leu Val Gln Arg Lys Thr Asp
                260                 265                 270

Gly Lys Ile Tyr Ala Leu Lys Ser Leu Ile Lys Thr Glu Met Phe Lys
                275                 280                 285

Lys Asp Gln Leu Ala His Val Arg Ala Glu Arg Asp Ile Leu Ala Asp
                290                 295                 300

Ser Lys Asp Asn Pro Trp Leu Val Lys Leu His Ala Ser Phe Gln Asp
305                 310                 315                 320

Thr Ala Tyr Leu Tyr Leu Leu Met Glu Phe Leu Pro Gly Gly Asp Leu
                325                 330                 335

Met Thr Met Leu Ile Lys Tyr Glu Ile Phe Ser Glu Asp Ile Thr Arg
                340                 345                 350

Phe Tyr Met Ala Glu Ile Val Met Ala Ile Glu Ala Val His Lys Leu
                355                 360                 365

Gly Phe Leu His Arg Asp Ile Lys Pro Asp Asn Ile Leu Leu Asp Arg
                370                 375                 380

Gly Gly His Val Lys Leu Thr Asp Phe Gly Leu Ser Thr Gly Gly Lys
385                 390                 395                 400

Lys Thr His Asp Asn Ser Tyr Tyr Gln Asn Leu Leu Lys Asn Ser Thr
                405                 410                 415

Ser Lys Asp Lys Asn Arg Asn Ser Gly Tyr Phe Asn Asp Ala Ile Asn
                420                 425                 430
```

-continued

```
Leu Thr Val Ser Asn Arg Gly Gln Ile Asn Thr Trp Arg Lys Ser Arg
            435                 440                 445

Arg Ala Met Ala Tyr Ser Thr Val Gly Thr Pro Asp Tyr Ile Ala Pro
    450                 455                 460

Glu Ile Phe Asn Gly Gln Gly Tyr Thr Tyr Leu Cys Asp Trp Trp Ser
465                 470                 475                 480

Val Gly Ala Ile Met Phe Glu Cys Leu Val Gly Trp Pro Pro Phe Cys
                485                 490                 495

Ala Glu Asp Thr Thr Asp Thr Tyr Arg Lys Ile Val Asn Trp Arg Glu
            500                 505                 510

Cys Leu Tyr Phe Pro Glu Glu Leu Thr Leu Ser Arg Asp Ser Glu Gly
        515                 520                 525

Leu Ile Arg Ser Phe Leu Cys Asp Ala Glu His Arg Ile Gly Ser Asp
    530                 535                 540

Gly Gly Gln Phe Gly Gly Ala Thr Gln Ile Lys Asn His Pro Phe Phe
545                 550                 555                 560

Arg Gly Val Val Trp Glu Gln Leu Arg Ser Ile Arg Ala Pro Phe Glu
                565                 570                 575

Pro Arg Leu Ser Ser Asn Ile Asp Val Ser Tyr Phe Pro Ile Asp Glu
            580                 585                 590

Ile Pro Gln Glu Asp Thr Ser Ala Ile His Arg Ala Gln Ala Arg Ala
        595                 600                 605

Lys Pro Asp Glu Gln Glu Ala Glu Met Ser Leu Pro Phe Ile Gly Tyr
    610                 615                 620

Thr Tyr Lys Ala Phe Asn Ala Phe Gln Gly Asn
625                 630                 635
```

<210> SEQ ID NO 17
<211> LENGTH: 637
<212> TYPE: PRT
<213> ORGANISM: Aspergillus niger

<400> SEQUENCE: 17

```
Met Asp Pro Asn Asn Asn Arg Pro His Leu Asn Phe Gly Tyr Asn Glu
1               5                   10                  15

Arg Ala Phe Asn Pro Ala Ala Asn Asn Arg Ala Tyr Pro Thr Thr
            20                  25                  30

Pro Ser Ala Phe Pro Gln Pro Ile Tyr Gln Ser Gln Ser Pro Gln Asp
        35                  40                  45

Tyr Met Asp Ala Gln Asn Gly Val Tyr Gly Gln Gly Tyr Phe Met Pro
    50                  55                  60

Asn Asn Tyr Pro Ala Gln Ala Tyr Ala Gln Pro His Tyr Gly Gln
65                  70                  75                  80

Pro Asn Leu Gln Ser Pro Gln Pro Ala Tyr Gln Ser Arg Met Gly Tyr
                85                  90                  95

Asn Val Ser Pro Asn Asp Gly Thr Asn Gly Leu Ile Gln Gln Phe Ser
            100                 105                 110

Asn Gln Asp Leu Asn Ser Asn Arg Thr Gly Phe Phe Asn Arg Ser Ala
        115                 120                 125

Ser Pro Ala Gln Arg Pro Arg Thr Ala Gly Asn Thr Ala Pro Gly Gln
    130                 135                 140

Gln Gln Gln Pro Gly His Leu Ala Pro Val Pro Arg Ser Pro Arg
145                 150                 155                 160

Leu Pro Pro Glu Asn Glu Glu Leu Gln Arg Tyr Pro Glu Arg Phe Ser
```

-continued

```
                165                 170                 175
Glu Asn Val His Lys Arg Gly Lys Ala Ala Lys Glu Leu Val Asn Val
            180                 185                 190

Phe Phe His Glu Asn Ile Glu Arg Ala Arg Asp Arg Asn Met Arg Ser
        195                 200                 205

Ala Glu Leu Asp Lys Met Met Arg Asp Pro Asn Ile Ser Gln Asp Ala
    210                 215                 220

Lys Val Lys Glu Ala Glu Met Val Gly Lys Lys Glu Ser Thr Phe Leu
225                 230                 235                 240

Arg Phe Leu Arg Thr Pro Glu Thr Pro Ala Asn Phe Gln Thr Ile Lys
                245                 250                 255

Ile Ile Gly Lys Gly Ala Phe Gly Glu Val Lys Leu Val Gln Arg Lys
            260                 265                 270

Ser Asp Asn Lys Ile Tyr Ala Leu Lys Ser Leu Ile Lys Ser Glu Met
        275                 280                 285

Phe Lys Lys Asp Gln Leu Ala His Val Arg Ala Glu Arg Asp Ile Leu
    290                 295                 300

Ala Asp Ser Lys Asp Asn Pro Trp Leu Val Lys Leu His Ala Ser Phe
305                 310                 315                 320

Gln Asp Pro Ala Tyr Leu Tyr Leu Leu Met Glu Phe Leu Pro Gly Gly
                325                 330                 335

Asp Leu Met Thr Met Leu Ile Lys Tyr Glu Ile Phe Ser Glu Asp Ile
            340                 345                 350

Thr Arg Phe Tyr Met Ala Glu Ile Val Met Ala Ile Glu Ala Val His
        355                 360                 365

Lys Leu Gly Phe Leu His Arg Asp Ile Lys Pro Asp Asn Ile Leu Leu
    370                 375                 380

Asp Arg Gly Gly His Val Lys Leu Thr Asp Phe Gly Leu Ser Thr Gly
385                 390                 395                 400

Gly Lys Lys Thr His Asp Asn Ser Tyr Tyr Gln Asn Leu Leu Lys Asn
                405                 410                 415

Ser Thr Ser Lys Asp Lys Asn Arg Asn Ser Gly Tyr Phe Asn Asp Ala
            420                 425                 430

Ile Asn Leu Thr Val Ser Asn Arg Gly Gln Ile Asn Thr Trp Arg Lys
        435                 440                 445

Ser Arg Arg Ala Met Ala Tyr Ser Thr Val Gly Thr Pro Asp Tyr Ile
    450                 455                 460

Ala Pro Glu Ile Phe Asn Gly Gln Gly Tyr Thr Tyr Leu Cys Asp Trp
465                 470                 475                 480

Trp Ser Val Gly Ala Ile Met Phe Glu Cys Leu Val Gly Trp Pro Pro
                485                 490                 495

Phe Cys Ala Glu Asp Thr Thr Asp Thr Tyr Arg Lys Ile Val Asn Trp
            500                 505                 510

Arg Glu Cys Leu Tyr Phe Pro Glu Glu Leu Thr Leu Ser Arg Glu Ser
        515                 520                 525

Glu Gly Leu Ile Arg Ser Phe Leu Cys Asp Ala Glu His Arg Ile Gly
    530                 535                 540

Asn Glu Gly Gly Gln Tyr Gly Gly Ala Thr Gln Ile Lys Asn His Pro
545                 550                 555                 560

Phe Phe Arg Gly Val Val Trp Asp Gln Leu Arg Lys Ile Arg Ala Pro
                565                 570                 575

Phe Glu Pro Arg Leu Thr Ser Asn Ile Asp Val Ser Tyr Phe Pro Ile
            580                 585                 590
```

```
Asp Glu Ile Pro Gln Glu Asp Thr Ser Ala Ile His Arg Ala Gln Ala
            595                 600                 605

Arg Ala Met Pro Asp Glu Gln Asn Ala Glu Met Ser Leu Pro Phe Ile
        610                 615                 620

Gly Tyr Thr Tyr Lys Ala Phe Asn Ala Phe Gln Ala Ser
625                 630                 635

<210> SEQ ID NO 18
<211> LENGTH: 620
<212> TYPE: PRT
<213> ORGANISM: Neurospora crassa

<400> SEQUENCE: 18

Met Asp Asn Thr Asn Arg Pro His Leu Asn Leu Gly Thr Asn Asp Thr
 1               5                  10                  15

Arg Met Ala Pro Asn Asp Arg Thr Tyr Pro Thr Thr Pro Ser Thr Phe
            20                  25                  30

Pro Gln Pro Val Phe Pro Gly Gln Ala Gly Gly Ser Gln Gln Tyr
        35                  40                  45

Asn Gln Ala Tyr Ala Gln Ser Gly Asn Tyr Tyr Gln Gln Asn His Asn
    50                  55                  60

Asp Pro Asn Thr Gly Leu Ala His Gln Phe Ala His Gln Asn Ile Gly
 65                 70                  75                  80

Ser Ala Gly Arg Ala Ser Pro Tyr Gly Ser Arg Gly Pro Ser Pro Ala
                85                  90                  95

Gln Arg Pro Arg Thr Ser Gly Asn Ser Gly Gln Gln Thr Tyr Gly
            100                 105                 110

Asn Tyr Leu Ser Ala Pro Met Pro Ser Asn Thr Gln Thr Glu Phe Ala
        115                 120                 125

Pro Leu Pro Ser Gly Thr Pro Thr Asn Met Ala Pro Met Pro Thr Thr
    130                 135                 140

Thr Arg Arg Ser Ala His Ser Trp Pro Leu Thr Ser Leu Arg Thr Ala
145                 150                 155                 160

Ser Ser Ala Pro Gly Ser Ala Thr Arg Gly Glu Cys Cys Ser Asp Ala
                165                 170                 175

Leu Leu Pro Leu His Pro Ala Val Ile Gly Ala Asp Thr Leu Phe Arg
            180                 185                 190

Gln Ser Glu Met Glu Gln Lys Leu Gly Glu Thr Asn Asp Ala Arg Arg
        195                 200                 205

Arg Glu Ser Ile Trp Ser Thr Ala Gly Arg Lys Glu Gly Gln Tyr Leu
    210                 215                 220

Arg Phe Leu Arg Thr Lys Asp Lys Pro Glu Asn Tyr Gln Thr Ile Lys
225                 230                 235                 240

Ile Ile Gly Lys Gly Ala Phe Gly Glu Val Lys Leu Val Gln Lys Lys
                245                 250                 255

Ala Asp Gly Lys Val Tyr Ala Met Lys Ser Leu Ile Lys Thr Glu Met
            260                 265                 270

Phe Lys Lys Asp Gln Leu Ala His Val Arg Ala Glu Arg Asp Ile Leu
        275                 280                 285

Ala Glu Ser Asp Ser Pro Trp Val Val Lys Leu Tyr Thr Thr Phe Gln
    290                 295                 300

Asp Ala Asn Phe Leu Tyr Met Leu Met Glu Phe Leu Pro Gly Gly Asp
305                 310                 315                 320

Leu Met Thr Met Leu Ile Lys Tyr Glu Ile Phe Ser Glu Asp Ile Thr
```

-continued

```
                325                 330                 335
Arg Phe Tyr Ile Ala Glu Ile Val Leu Ala Ile Asp Ala Val His Lys
            340                 345                 350

Leu Gly Phe Ile His Arg Asp Ile Lys Pro Asp Asn Ile Leu Leu Asp
        355                 360                 365

Arg Gly Gly His Val Lys Leu Thr Asp Phe Gly Leu Ser Thr Gly Phe
    370                 375                 380

His Lys Leu His Asp Asn Asn Tyr Tyr Thr Gln Leu Leu Gln Gly Lys
385                 390                 395                 400

Ser Asn Lys Pro Arg Asp Asn Arg Asn Ser Val Ala Ile Asp Gln Ile
                405                 410                 415

Asn Leu Thr Val Ser Asn Arg Ala Gln Ile Asn Asp Trp Arg Arg Ser
            420                 425                 430

Arg Arg Leu Met Ala Tyr Ser Thr Val Gly Thr Pro Asp Tyr Ile Ala
        435                 440                 445

Pro Glu Ile Phe Thr Gly His Gly Tyr Ser Phe Asp Cys Asp Trp Trp
    450                 455                 460

Ser Leu Gly Thr Ile Met Phe Glu Cys Leu Val Gly Trp Pro Pro Phe
465                 470                 475                 480

Cys Ala Glu Asp Ser His Asp Thr Tyr Arg Lys Ile Val Asn Trp Arg
                485                 490                 495

His Ser Leu Tyr Phe Pro Asp Asp Ile Thr Leu Gly Val Asp Ala Glu
            500                 505                 510

Asn Leu Ile Arg Ser Leu Ile Cys Asn Thr Glu Asn Arg Leu Gly Arg
        515                 520                 525

Gly Gly Ala His Glu Ile Lys Ser His Ala Phe Phe Arg Gly Val Glu
    530                 535                 540

Phe Asp Ser Leu Arg Arg Ile Arg Ala Pro Phe Glu Pro Arg Leu Thr
545                 550                 555                 560

Ser Ala Ile Asp Thr Thr Tyr Phe Pro Thr Asp Glu Ile Asp Gln Thr
                565                 570                 575

Asp Asn Ala Thr Leu Leu Lys Ala Gln Gln Ala Ala Arg Gly Ala Ala
            580                 585                 590

Ala Pro Ala Gln Gln Glu Glu Ser Pro Glu Leu Ser Leu Pro Phe Ile
        595                 600                 605

Gly Tyr Thr Phe Lys Arg Phe Asp Asn Asn Phe Arg
    610                 615                 620

<210> SEQ ID NO 19
<211> LENGTH: 665
<212> TYPE: PRT
<213> ORGANISM: Colletotrichum trifolii

<400> SEQUENCE: 19

Met Asp Asn Asn Asn Asn Arg Leu Tyr Leu Asn Ile Gly Asn Asn Asn
 1               5                  10                  15

Asp Arg Leu Gly Pro Gly Ser Asp Arg Gln Tyr Pro Thr Thr Pro Ser
            20                  25                  30

Thr Phe Pro Gln Pro Val Phe Pro His Gln Gly Gln Gln Gln Gln Gln
        35                  40                  45

Gln Gln Gln Gln Gln Leu His His Gln Gln Gln Pro Gly Met Gln His
    50                  55                  60

Pro Gln Gln Tyr Gln Ala Gln Gln Gln Gln Gln Gln Gln Gln Gln Gln
65                  70                  75                  80
```

-continued

```
Gln Gln Gln Gln Pro Tyr Gln Thr Gly Tyr Ala Pro Ser Gly Tyr Phe
            85                  90                  95

Asn Pro Asn Gln Gln Ala Ala Gln Tyr Pro Pro Gln Gly His Gly Asp
            100                 105                 110

Tyr Asn Ala Ala Tyr Gln Pro Arg Ser Asn Thr Pro Gly Thr Asn Asp
            115                 120                 125

Pro Asn Val Gly Leu Ala His Gln Phe Ser His Gln Asn Leu Gly Gly
            130                 135                 140

Ala Ala Arg Ala Ser Pro Tyr Gly Ser Arg Gly Pro Ser Pro Gly Gln
145                 150                 155                 160

Arg Pro Arg Thr Ala Gly Ala Ser Gly Gln Pro Pro Ser Gly Tyr Gly
            165                 170                 175

His Tyr Ala Thr Pro Pro Leu Pro Asn Gln Gln Pro Ala Ser Val Asp
            180                 185                 190

Pro Phe Ala Pro Ala Pro Glu Arg Asn Tyr Glu Lys Tyr Gly Pro Asn
            195                 200                 205

Ala Asn Gly Asn Gln Lys Lys Cys Thr Gln Leu Ala Ser Asp Phe Phe
            210                 215                 220

Lys Asp Ser Val Lys Arg Ala Arg Glu Arg Asn Gln Arg Gln Ser Glu
225                 230                 235                 240

Met Glu Ala Lys Leu Ser Glu Pro Asn Gln Ser Gln Ser Arg Arg Glu
            245                 250                 255

Gln Ile Trp Ser Thr Ala Gly Arg Lys Glu Gly Gln Tyr Leu Arg Phe
            260                 265                 270

Leu Arg Thr Lys Asp Lys Pro Glu Asn Tyr Asn Thr Val Lys Ile Ile
            275                 280                 285

Gly Lys Gly Ala Phe Gly Glu Val Lys Leu Val Gln Lys Lys Gly Asp
            290                 295                 300

Gly Lys Val Tyr Ala Met Lys Ser Leu Ile Lys Thr Glu Met Phe Lys
305                 310                 315                 320

Lys Asp Gln Leu Ala His Val Arg Ser Glu Arg Asp Ile Leu Ala Glu
            325                 330                 335

Ser Asp Ser Pro Trp Val Val Lys Leu Tyr Thr Thr Phe Gln Asp Ser
            340                 345                 350

Tyr Phe Leu Tyr Met Leu Met Glu Phe Leu Pro Gly Gly Asp Leu Met
            355                 360                 365

Thr Met Leu Ile Lys Tyr Glu Ile Phe Ser Glu Asp Ile Thr Arg Phe
            370                 375                 380

Tyr Ile Ala Glu Ile Val Leu Ala Ile Glu Ala Val His Lys Leu Gly
385                 390                 395                 400

Phe Ile His Arg Asp Ile Lys Pro Asp Asn Ile Leu Leu Asp Arg Gly
            405                 410                 415

Gly His Val Lys Leu Thr Asp Phe Gly Leu Ser Thr Gly Phe Asn Arg
            420                 425                 430

Leu His Asp Asn Asn Tyr Tyr Gln Gln Leu Leu Gln Gly Arg Ser Asn
            435                 440                 445

Lys Pro Arg Asp Arg Asn Ser Val Ala Ile Asp Gln Ile Asn Leu Thr
            450                 455                 460

Val Ser Asn Arg Ser Gln Ile Asn Asp Trp Arg Arg Ser Arg Arg Leu
465                 470                 475                 480

Met Ala Tyr Ser Thr Val Gly Thr Pro Asp Tyr Ile Ala Pro Glu Ile
            485                 490                 495

Phe Thr Gly His Gly Tyr Thr Phe Asp Cys Asp Trp Trp Ser Leu Gly
```

```
                    500                 505                 510
Thr Ile Met Phe Glu Cys Leu Val Gly Trp Pro Pro Phe Cys Ala Glu
            515                 520                 525

Asp Ser His Asp Thr Tyr Arg Lys Ile Val Asn Trp Arg Gln Thr Leu
        530                 535                 540

Tyr Phe Pro Asp Asp Ile Gln Leu Gly Val Glu Ala Glu Asn Leu Ile
545                 550                 555                 560

Arg Ser Leu Ile Cys Asn Thr Glu Asn Arg Leu Gly Arg Ser Gly Ala
                565                 570                 575

His Glu Ile Lys Ala His Ser Phe Phe Arg Gly Val Glu Phe Asp Ser
            580                 585                 590

Leu Arg Arg Ile Arg Ala Pro Phe Glu Pro Arg Leu Thr Ser Ala Ile
            595                 600                 605

Asp Thr Thr Tyr Phe Pro Thr Asp Glu Ile Asp Gln Thr Asp Asn Ala
            610                 615                 620

Thr Val Leu Lys Ala Gln Ala Ile Gln Gln Ala Arg Ser Gly Ile Pro
625                 630                 635                 640

Gln Val Glu Glu Ser Pro Glu Met Ser Leu Pro Phe Ile Gly Tyr Thr
                645                 650                 655

Phe Lys Arg Phe Asp Asn Asn Phe Arg
            660                 665

<210> SEQ ID NO 20
<211> LENGTH: 756
<212> TYPE: PRT
<213> ORGANISM: Saccharomyces cerevisiae

<400> SEQUENCE: 20

Met Tyr Asn Ser Ser Thr Asn His His Glu Gly Ala Pro Thr Ser Gly
  1               5                  10                  15

His Gly Tyr Tyr Met Ser Gln Gln Gln Asp Gln Gln His Gln Gln Gln
             20                  25                  30

Gln Gln Tyr Ala Asn Glu Met Asn Pro Tyr Gln Gln Ile Pro Arg Pro
         35                  40                  45

Pro Ala Ala Gly Phe Ser Ser Asn Tyr Met Lys Glu Gln Gly Ser His
     50                  55                  60

Gln Ser Leu Gln Glu His Leu Gln Arg Glu Thr Gly Asn Leu Gly Ser
 65                  70                  75                  80

Gly Phe Thr Asp Val Pro Ala Leu Asn Tyr Pro Ala Thr Pro Pro Pro
                 85                  90                  95

His Asn Asn Tyr Ala Ala Ser Asn Gln Met Ile Asn Thr Pro Pro Pro
            100                 105                 110

Ser Met Gly Gly Leu Tyr Arg His Asn Asn Asn Ser Gln Ser Met Val
        115                 120                 125

Gln Asn Gly Asn Gly Ser Gly Asn Ala Gln Leu Pro Gln Leu Ser Pro
    130                 135                 140

Gly Gln Tyr Ser Ile Glu Ser Glu Tyr Asn Gln Asn Leu Asn Gly Ser
145                 150                 155                 160

Ser Ser Ser Ser Pro Phe His Gln Pro Gln Thr Leu Arg Ser Asn Gly
                165                 170                 175

Ser Tyr Ser Ser Gly Leu Arg Ser Val Lys Ser Phe Gln Arg Leu Gln
            180                 185                 190

Gln Glu Gln Glu Asn Val Gln Val Gln Gln Leu Ser Gln Ala Gln
        195                 200                 205
```

```
Gln Gln Asn Ser Arg Gln Gln Gln Gln Leu Gln Tyr Gln Gln Gln
    210                 215                 220
Gln Gln Gln Gln Gln Gln Gln His Met Gln Ile Gln Gln Gln Gln
225                 230                 235                 240
Gln Gln Gln Gln Gln Gln Gln Ser Gln Ser Pro Val Gln Ser Gly
                245                 250                 255
Phe Asn Asn Gly Thr Ile Ser Asn Tyr Met Tyr Phe Glu Arg Arg Pro
            260                 265                 270
Asp Leu Leu Thr Lys Gly Thr Gln Asp Lys Ala Ala Ala Val Lys Leu
            275                 280                 285
Lys Ile Glu Asn Phe Tyr Gln Ser Ser Val Lys Tyr Ala Ile Glu Arg
            290                 295                 300
Asn Glu Arg Arg Val Glu Leu Glu Thr Glu Leu Thr Ser His Asn Trp
305                 310                 315                 320
Ser Glu Glu Arg Lys Ser Arg Gln Leu Ser Ser Leu Gly Lys Lys Glu
                325                 330                 335
Ser Gln Phe Leu Arg Leu Arg Arg Thr Arg Leu Ser Leu Glu Asp Phe
            340                 345                 350
His Thr Val Lys Val Ile Gly Lys Gly Ala Phe Gly Glu Val Arg Leu
            355                 360                 365
Val Gln Lys Lys Asp Thr Gly Lys Ile Tyr Ala Met Lys Thr Leu Leu
370                 375                 380
Lys Ser Glu Met Tyr Lys Lys Asp Gln Leu Ala His Val Lys Ala Glu
385                 390                 395                 400
Arg Asp Val Leu Ala Gly Ser Asp Ser Pro Trp Val Val Ser Leu Tyr
                405                 410                 415
Tyr Ser Phe Gln Asp Ala Gln Tyr Leu Tyr Leu Ile Met Glu Phe Leu
            420                 425                 430
Pro Gly Gly Asp Leu Met Thr Met Leu Ile Arg Trp Gln Leu Phe Thr
        435                 440                 445
Glu Asp Val Thr Arg Phe Tyr Met Ala Glu Cys Ile Leu Ala Ile Glu
    450                 455                 460
Thr Ile His Lys Leu Gly Phe Ile His Arg Asp Ile Lys Pro Asp Asn
465                 470                 475                 480
Ile Leu Ile Asp Ile Arg Gly His Ile Lys Leu Ser Asp Phe Gly Leu
                485                 490                 495
Ser Thr Gly Phe His Lys Thr His Asp Ser Asn Tyr Tyr Lys Lys Leu
            500                 505                 510
Leu Gln Gln Asp Glu Ala Thr Asn Gly Ile Ser Lys Pro Gly Thr Tyr
        515                 520                 525
Asn Ala Asn Thr Thr Asp Thr Ala Asn Lys Arg Gln Thr Met Val Val
    530                 535                 540
Asp Ser Ile Ser Leu Thr Met Ser Asn Arg Gln Gln Ile Gln Thr Trp
545                 550                 555                 560
Arg Lys Ser Arg Arg Leu Met Ala Tyr Ser Thr Val Gly Thr Pro Asp
                565                 570                 575
Tyr Ile Ala Pro Glu Ile Phe Leu Tyr Gln Gly Tyr Gly Gln Glu Cys
            580                 585                 590
Asp Trp Trp Ser Leu Gly Ala Ile Met Tyr Glu Cys Leu Ile Gly Trp
        595                 600                 605
Pro Pro Phe Cys Ser Glu Thr Pro Gln Glu Thr Tyr Arg Lys Ile Met
    610                 615                 620
Asn Phe Glu Gln Thr Leu Gln Phe Pro Asp Asp Ile His Ile Ser Tyr
```

-continued

```
            625                 630                 635                 640
Glu Ala Glu Asp Leu Ile Arg Arg Leu Leu Thr His Ala Asp Gln Arg
                    645                 650                 655
Leu Gly Arg His Gly Gly Ala Asp Glu Ile Lys Ser His Pro Phe Phe
                660                 665                 670
Arg Gly Val Asp Trp Asn Thr Ile Arg Gln Val Glu Ala Pro Tyr Ile
                675                 680                 685
Pro Lys Leu Ser Ser Ile Thr Asp Thr Arg Phe Phe Pro Thr Asp Glu
                690                 695                 700
Leu Glu Asn Val Pro Asp Ser Pro Ala Met Ala Gln Ala Ala Lys Gln
705                 710                 715                 720
Arg Glu Gln Met Thr Lys Gln Gly Gly Ser Ala Pro Val Lys Glu Asp
                725                 730                 735
Leu Pro Phe Ile Gly Tyr Thr Tyr Ser Arg Phe Asp Tyr Leu Thr Arg
                740                 745                 750
Lys Asn Ala Leu
            755

<210> SEQ ID NO 21
<211> LENGTH: 639
<212> TYPE: PRT
<213> ORGANISM: Homo sapiens

<400> SEQUENCE: 21

Met Gly Gly His Phe Trp Pro Glu Pro Tyr Thr Val Phe Met Trp
1               5                   10                  15
Gly Ser Pro Trp Glu Ala Asp Ser Pro Arg Val Lys Leu Arg Gly Arg
                20                  25                  30
Glu Lys Gly Arg Gln Thr Glu Gly Gly Ala Phe Pro Leu Val Ser Ser
            35                  40                  45
Ala Leu Ser Gly Asp Pro Arg Phe Phe Ser Pro Thr Thr Pro Pro Ala
        50                  55                  60
Glu Pro Ile Val Val Arg Leu Lys Glu Val Arg Leu Gln Arg Asp Asp
65                  70                  75                  80
Phe Glu Ile Leu Lys Val Ile Gly Arg Gly Ala Phe Ser Glu Val Ala
                85                  90                  95
Val Val Lys Met Lys Gln Thr Gly Gln Val Tyr Ala Met Lys Ile Met
                100                 105                 110
Asn Lys Trp Asp Met Leu Lys Arg Gly Glu Val Ser Cys Phe Arg Glu
            115                 120                 125
Glu Arg Asp Val Leu Val Asn Gly Asp Arg Arg Trp Ile Thr Gln Leu
        130                 135                 140
His Phe Ala Phe Gln Asp Glu Asn Tyr Leu Tyr Leu Val Met Glu Tyr
145                 150                 155                 160
Tyr Val Gly Gly Asp Leu Leu Thr Leu Leu Ser Lys Phe Gly Glu Arg
                165                 170                 175
Ile Pro Ala Glu Met Ala Arg Phe Tyr Leu Ala Glu Ile Val Met Ala
                180                 185                 190
Ile Asp Ser Val His Arg Leu Gly Tyr Val His Arg Asp Ile Lys Pro
            195                 200                 205
Asp Asn Ile Leu Leu Asp Arg Cys Gly His Ile Arg Leu Ala Asp Phe
        210                 215                 220
Gly Ser Cys Leu Lys Leu Arg Ala Asp Gly Thr Val Arg Ser Leu Val
225                 230                 235                 240
```

```
Ala Val Gly Thr Pro Asp Tyr Leu Ser Pro Glu Ile Leu Gln Ala Val
            245                 250                 255
Gly Gly Gly Pro Gly Thr Gly Ser Tyr Gly Pro Glu Cys Asp Trp Trp
        260                 265                 270
Ala Leu Gly Val Phe Ala Tyr Glu Met Phe Tyr Gly Gln Thr Pro Phe
            275                 280                 285
Tyr Ala Asp Ser Thr Ala Glu Thr Tyr Gly Lys Ile Val His Tyr Lys
        290                 295                 300
Glu His Leu Ser Leu Pro Leu Val Asp Glu Gly Val Pro Glu Glu Ala
305                 310                 315                 320
Arg Asp Phe Ile Gln Arg Leu Leu Cys Pro Pro Glu Thr Arg Leu Gly
                325                 330                 335
Arg Gly Gly Ala Gly Asp Phe Arg Thr His Pro Phe Phe Gly Leu
            340                 345                 350
Asp Trp Asp Gly Leu Arg Asp Ser Val Pro Pro Phe Thr Pro Asp Phe
        355                 360                 365
Glu Gly Ala Thr Asp Thr Cys Asn Phe Asp Leu Val Glu Asp Gly Leu
    370                 375                 380
Thr Ala Met Val Ser Gly Gly Glu Thr Leu Ser Asp Ile Arg Glu
385                 390                 395                 400
Gly Ala Pro Leu Gly Val His Leu Pro Phe Val Gly Tyr Ser Tyr Ser
                405                 410                 415
Cys Met Ala Leu Arg Asp Ser Glu Val Pro Gly Pro Thr Pro Met Glu
            420                 425                 430
Val Glu Ala Glu Gln Leu Leu Glu Pro His Val Gln Ala Pro Ser Leu
        435                 440                 445
Glu Pro Ser Val Ser Pro Gln Asp Glu Thr Ala Glu Val Ala Val Pro
    450                 455                 460
Ala Ala Val Pro Ala Ala Glu Ala Glu Ala Glu Val Thr Leu Arg Glu
465                 470                 475                 480
Leu Gln Glu Ala Leu Glu Glu Glu Val Leu Thr Arg Gln Ser Leu Ser
                485                 490                 495
Arg Glu Met Glu Ala Ile Arg Thr Asp Asn Gln Asn Phe Ala Ser Gln
            500                 505                 510
Leu Arg Glu Ala Glu Ala Arg Asn Arg Asp Leu Glu Ala His Val Arg
        515                 520                 525
Gln Leu Gln Glu Arg Met Glu Leu Leu Gln Ala Glu Gly Ala Thr Ala
    530                 535                 540
Val Thr Gly Val Pro Ser Pro Arg Ala Thr Asp Pro Pro Ser His Leu
545                 550                 555                 560
Asp Gly Pro Pro Ala Val Ala Val Gly Gln Cys Pro Leu Val Gly Pro
                565                 570                 575
Gly Pro Met His Arg Arg His Leu Leu Leu Pro Ala Arg Val Pro Arg
            580                 585                 590
Pro Gly Leu Ser Glu Ala Leu Ser Leu Leu Phe Ala Val Val Leu
        595                 600                 605
Ser Arg Ala Ala Ala Leu Gly Cys Ile Gly Leu Val Ala His Ala Gly
    610                 615                 620
Gln Leu Thr Ala Val Trp Arg Arg Pro Gly Ala Ala Arg Ala Pro
625                 630                 635

<210> SEQ ID NO 22
<211> LENGTH: 469
<212> TYPE: PRT
```

<213> ORGANISM: Schizosaccharomyces pombe

<400> SEQUENCE: 22

```
Met Asp Lys Asn Asp Tyr Leu His Phe Glu Arg Asn Pro Ser Leu Phe
 1               5                  10                  15
Pro Lys Ser Thr Leu Asp Lys Val Gln Lys Thr Lys Lys Tyr Ile Glu
                20                  25                  30
His Tyr Tyr Lys Val Ala Val Asp His Ala Val Glu Arg Asn Gln Arg
            35                  40                  45
Arg Ile Asn Leu Glu Gln Arg Leu Ala Thr Glu Arg Gly Ser Glu Glu
        50                  55                  60
Arg Lys Asn Arg Gln Leu Arg Ala Ser Gly Glu Lys Glu Ser Gln Phe
65                  70                  75                  80
Leu Arg Phe Arg Arg Thr Arg Leu Ser Leu Glu Asp Phe Ser Thr Ile
                85                  90                  95
Lys Val Ile Gly Lys Gly Ala Phe Gly Glu Val Arg Leu Val Gln Lys
            100                 105                 110
Leu Asp Thr Gly Lys Ile Tyr Ala Met Lys Ser Leu Leu Lys Thr Glu
        115                 120                 125
Met Phe Lys Arg Asp Gln Leu Ala His Val Lys Ala Glu Arg Asp Leu
130                 135                 140
Leu Val Glu Ser Asp Ser Pro Trp Val Val Ser Leu Tyr Tyr Ala Phe
145                 150                 155                 160
Gln Asp Ser Leu Tyr Leu Tyr Leu Ile Met Glu Phe Leu Pro Gly Gly
                165                 170                 175
Asp Leu Met Thr Met Leu Ile Asn Tyr Asp Thr Phe Ser Glu Asp Val
            180                 185                 190
Thr Arg Phe Tyr Met Ala Glu Cys Val Leu Ala Ile Ala Asp Val His
        195                 200                 205
Arg Met Gly Tyr Ile His Arg Asp Ile Lys Pro Asp Asn Ile Leu Ile
    210                 215                 220
Asp Arg Asp Gly His Ile Lys Leu Ser Asp Phe Gly Leu Ser Thr Gly
225                 230                 235                 240
Phe Tyr Lys Gln Asp Gln Ser Ala Ser Tyr Met Lys Pro Arg Thr Gly
                245                 250                 255
Asn Thr Val Lys Arg Gly Gln Met Val Asp Ala Ile Trp Leu Thr Met
            260                 265                 270
Ser Ser Lys Asp Lys Met Ala Thr Trp Lys Lys Asn Arg Arg Val Met
        275                 280                 285
Ala Tyr Ser Thr Val Gly Thr Pro Asp Tyr Ile Ala Pro Glu Ile Phe
    290                 295                 300
Leu Gln Gln Gly Tyr Gly Gln Asp Cys Asp Trp Trp Ser Leu Gly Ala
305                 310                 315                 320
Ile Met Phe Glu Cys Leu Ile Gly Trp Pro Pro Phe Cys Ser Glu Asn
                325                 330                 335
Ser His Glu Thr Tyr Arg Lys Ile Ile Asn Trp Arg Glu Thr Leu Thr
            340                 345                 350
Phe Pro Asn Asp Ile His Leu Ser Ile Glu Ala Arg Asp Leu Met Asp
        355                 360                 365
Arg Leu Met Thr Asp Ser Glu His Arg Leu Gly Arg Gly Gly Ala Ile
    370                 375                 380
Glu Ile Met Gln His Pro Phe Phe Thr Gly Ile Asp Trp Asp His Ile
385                 390                 395                 400
```

```
Arg Glu Thr Ala Ala Pro Phe Ile Pro Asn Leu Lys Ser Ile Thr Asp
            405                 410                 415

Thr His Tyr Phe Pro Val Asp Glu Leu Glu Gln Val Pro Glu Gln Pro
            420                 425                 430

Val Thr Gln Gln Pro Ala Ser Val Asp Pro Gln Thr Leu Glu Gln Thr
            435                 440                 445

Asn Leu Ala Phe Leu Gly Tyr Thr Tyr Lys Lys Phe Asn Tyr Leu Thr
450                 455                 460

Met Lys Gly Ala Leu
465

<210> SEQ ID NO 23
<211> LENGTH: 551
<212> TYPE: PRT
<213> ORGANISM: Aspergillus niger

<400> SEQUENCE: 23

Met Asp Pro Asn Asn Asn Arg Leu His Leu Asn Phe Gly Tyr Asn
1               5                   10                  15

Asp Arg Gly Phe Asn Ala Ala Ala Asn Asn Arg Ala Tyr Pro Thr
            20                  25                  30

Thr Pro Ser Ala Phe Pro Gln Pro Ile Tyr Gln Asn Gln Gly Pro Gln
            35                  40                  45

Asp Tyr Met Asp Ala Gln Asn Gly Ala Tyr Ala Gln Gly Gly Tyr Phe
50                  55                  60

Met Ala Asn Pro Tyr Gln Ala Gln Ala Ala Tyr Gly Gln Pro His Tyr
65                  70                  75                  80

Gly Gln Asn Leu Gln Ser Pro Gln Pro Ala Tyr Pro Ser Arg Met Gly
            85                  90                  95

Tyr Ser Ala Asn Asp Gly Thr Asn Gly Leu Ile Gln Gln Phe Ser Asn
            100                 105                 110

Gln Asp Leu Asn Ser Pro Arg Ser Gly Phe Phe Ala Arg Ser Ala Ser
            115                 120                 125

Pro Ala Gln Arg Pro Arg Thr Ala Gly Ser Pro Ala Pro Gly Gln Gln
    130                 135                 140

Gln Pro Gly His Leu Ala Pro Met Pro Arg Ser Pro Arg Thr Pro
145                 150                 155                 160

Ala Glu Asn Glu Glu Leu Gln Arg Tyr Pro Glu Arg Tyr Ser Glu Asn
                165                 170                 175

Val His Lys Arg Gly Lys Ala Ala Lys Glu Leu Val Ser Val Phe Phe
            180                 185                 190

Asn Glu Asn Asn Glu Arg Ala Arg Asp Arg Asn Met Arg Ser Ala Glu
            195                 200                 205

Leu Asp Lys Met Ile Arg Glu Pro Ser Ile Pro Lys Glu Asn Lys Cys
    210                 215                 220

Lys Asp Ala Glu Val Leu Ala Lys Lys Glu Ser Asn Phe Leu Arg Phe
225                 230                 235                 240

Leu Arg Thr Lys Glu Thr Pro Gln Asn Phe Gln Thr Ile Lys Ile Ile
                245                 250                 255

Gly Lys Gly Ala Phe Gly Glu Val Lys Leu Val Gln Arg Lys Ala Asp
            260                 265                 270

Gly Lys Ile Tyr Ala Leu Lys Ser Leu Ile Lys Thr Glu Met Phe Lys
    275                 280                 285

Gln Gly Pro Ala Ala His Val Arg Ala Glu Arg Asp Ile Leu Ala Asp
290                 295                 300
```

-continued

```
Ser Lys Asp Asn Pro Trp Leu Val Lys Leu His Ala Ser Phe Gln Asp
305                 310                 315                 320

Thr Ala Tyr Leu Tyr Leu Leu Met Glu Phe Leu Pro Gly Gly Asp Leu
                325                 330                 335

Met Thr Met Leu Ile Lys Tyr Glu Ile Phe Ser Glu Asp Ile Thr Arg
            340                 345                 350

Phe Tyr Met Ala Glu Ile Val Met Ala Ile Glu Ala Val His Lys Leu
            355                 360                 365

Gly Phe Leu His Arg Asp Ile Lys Pro Asp Asn Ile Leu Leu Asp Arg
    370                 375                 380

Gly Gly His Val Lys Leu Thr Asp Phe Gly Leu Ser Thr Gly Gly Lys
385                 390                 395                 400

Lys Thr His Asp Asn Ser Tyr Tyr Gln Asn Leu Leu Lys Asn Ser Thr
                405                 410                 415

Ser Lys Asp Lys Asn Arg Asn Ser Gly Tyr Phe Asn Asp Ala Ile Asn
            420                 425                 430

Leu Thr Val Ser Asn Arg Gly Gln Ile Asn Thr Trp Arg Lys Ser Arg
        435                 440                 445

Arg Ala Met Ala Tyr Ser Thr Val Gly Thr Pro Asp Tyr Ile Ala Pro
    450                 455                 460

Glu Ile Phe Asn Gly Gln Gly Tyr Thr Tyr Leu Cys Asp Trp Trp Ser
465                 470                 475                 480

Val Gly Ala Ile Met Phe Glu Cys Leu Val Gly Trp Pro Pro Phe Cys
            485                 490                 495

Ala Glu Asp Thr Thr Asp Thr Tyr Arg Lys Ile Val Asn Trp Arg Glu
            500                 505                 510

Cys Leu Tyr Phe Pro Glu Glu Leu Thr Leu Ser Arg Asp Ser Glu Gly
        515                 520                 525

Leu Ile Arg Ser Thr Lys Asn Ile Asp Gly Glu Val Lys Lys Glu Asp
        530                 535                 540

Ser Asp Pro Leu Gly Asn Gln
545                 550
```

REGULATABLE GROWTH OF FILAMENTOUS FUNGI

CROSS-REFERENCES TO RELATED APPLICATIONS

The present application is a Continuation of U.S. patent application Ser. No. 10/100,252, filed Mar. 14, 2002, now issued U.S. Pat. No. 6,936,449, which claims priority to 60/276,571 filed Mar. 15, 2001 and to 60/276,618, filed Mar. 14, 2001.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

Growth morphology is an important factor affecting fermentation of filamentous fungi during production of proteins and fine chemicals. cot-1 of *Neurospora crassa* is a colonial temperature sensitive mutation that has been described in detail Steele, et al., *Arch. Microbiol.* 113:43 (1977) and Collinge, et al., *Trans. Br. Mycol. Soc.* 71:102 (1978)). Germination and growth of the mutant is normal at 26° C., but a shift to 37° C. causes the cessation of hyphal tip extension, and emergence of lateral branches at an abnormally high frequency to give hyperbranching germlings. An increase in the frequency of septation is also seen. Sequence analysis indicated the gene product belongs to the family of serine/threonine protein kinases (Yarden, et al., *EMBO J.* 11:2159 (1992). These kinases act in signal transduction pathways, but how cot-1 is integrated into the pathway(s) controlling hyphal growth polarity has yet to be elucidated. The specific mutation that causes the temperature sensitivity in *N. crassa* cot-1 has been found to be a histidine to arginine substitution (Gorovits, et al., *Fungal Genetics and Biol.* 27:264 (1999).

There remains a need in the art for genes that control growth morphology in filamentous fungal cells, like *Trichoderma* and *Aspergillus*, that are used as a source of recombinant proteins in an industrial setting and to enhance the production of proteins and fine chemicals. This invention meets this need as well as others.

SUMMARY OF THE INVENTION

One embodiment of this invention provides for an isolated polynucleotide selected from the group consisting of a nucleic acid sequence that encodes or is complementary to a sequence that encodes a cotA polypeptide having at least 85% sequence identity to the amino acid sequence presented in any one of FIG. 2 (SEQ ID NO:2), FIG. 4 (SEQ ID NO:4) or FIG. 6 (SEQ ID NO:6); a nucleic acid sequence that encodes or is complementary to a sequence that encodes a cotA polypeptide having at least 90% sequence identity to the amino acid sequence presented in any one of FIG. 2 (SEQ ID NO:2), FIG. 4 (SEQ ID NO:4) or FIG. 6 (SEQ ID NO:6); a nucleic acid sequence that encodes or is complementary to a sequence that encodes a cotA polypeptide having at least 95% sequence identity to the amino acid sequence presented in any one of FIG. 2 (SEQ ID NO:2), FIG. 4 (SEQ ID NO:4) or FIG. 6 (SEQ ID NO:6); a nucleic acid sequence that encodes or is complementary to a sequence that encodes a cotA polypeptide having the amino acid sequence presented in any one of FIG. 2 (SEQ ID NO:2), FIG. 4 (SEQ ID NO:4) or FIG. 6 (SEQ ID NO:6); the nucleic acid sequence presented as any one of SEQ ID NOs:1, 3 or 5 (FIG. 1, 3 or 5, respectively) a portion greater than 200 bp thereof, or the complement thereof, and a nucleic acid sequence that hybridizes, under high stringency conditions to the sequence presented as any one of SEQ ID NOs:1, 3 or 5, or the complement or a fragment thereof, wherein said isolated polynucleotide, when induced in a fungal cell, causes said cell to grow more slowly.

In a first aspect of this embodiment, the % identity is calculated using the CLUSTAL-W program in MacVector version 6.5, operated with default parameters, including an open gap penalty of 10.0, an extended gap penalty of 0.1, and a BLOSUM 30 similarity matrix.

In a second aspect of this embodiment, hybridization is conducted at 42° C. in 50% formamide, 6×SSC, 5×Denhardt's solution, 0.5% SDS and 100 µg/ml denatured carrier DNA followed by washing two times in 2×SSPE and 0.5% SDS at room temperature and two additional times in 0.1× SSPE and 0.5% SDS at 42° C. In yet another embodiment, the isolated polynucleotide is an RNA molecule.

In a third aspect of this embodiment, the isolated polynucleotide is operably linked to a regulatable promoter. In a preferred aspect of this embodiment the promoter is induced by maltose in the fungal cell environment. In another preferred aspect of this embodiment, the polynucleotide is in the antisense orientation.

In a fourth aspect of this embodiment, the polynucleotide is SEQ ID NO:1.

In a fifth aspect of this embodiment, the polynucleotide is SEQ ID NO:3.

In a sixth aspect of this embodiment, the polynucleotide is SEQ ID NO:5.

In second embodiment of this invention, a recombinant filamentous fungal host cell comprising a cotA polynucleotide is provided. In one aspect of this embodiment, the fungal host cell is a member of *Aspergillus* spp. In another aspect of this embodiment, the cell is an *Aspergillus niger* fungal cell. In yet another aspect of this invention, the cell is a member of *Trichoderma*, more preferred is *T. reesei*. In further aspect of this embodiment, the recombinant fungal host cell is transformed with the vector comprising any one of SEQ ID NOs:1, 3 or 5 operably linked to a regulatable promoter. In a particularly preferred aspect of this embodiment, the vector integrates into the wild-type cotA gene. In another aspect of this embodiment, the vector integrates ectopically. In an aspect of this embodiment, the polynucleotide integrates in the antisense orientation.

In a third embodiment of this invention, a substantially purified cotA polypeptide with the biological activity of a serine/threonine kinase is provided. The biologically active polypeptide comprises a sequence selected from the group consisting of an amino acid sequence having at least 85% sequence identity to the amino acid sequence presented in any one of FIG. 2 (SEQ ID NO:2), FIG. 4 (SEQ ID NO:4) or FIG. 6 (SEQ ID NO:6); an amino acid sequence having at least 90% sequence identity to the amino acid sequence presented in any one of FIG. 2 (SEQ ID NO:2), FIG. 4 (SEQ ID NO:4) or FIG. 6 (SEQ ID NO:6); an amino acid sequence having at least 95% sequence identity to the amino acid sequence presented in any one of FIG. 2 (SEQ ID NO:2), FIG. 4 (SEQ ID NO:4) or FIG. 6 (SEQ ID NO:6); the amino acid sequence presented as any one of SEQ ID NOs:2, 4 or 6, a substantially purified biologically active fragment of the amino acid sequence presented as any one of SEQ ID NO:2, 4 or 6, and a substantially purified full length protein comprising the amino acid sequence encoded by either of SEQ ID NOs:13 or 14.

In a fourth embodiment of this invention, a purified antibody that specifically binds to a cotA polypeptide is provided. In one aspect of this embodiment, a polynucleotide is provided that encodes a cotA polypeptide that specifically binds to an antibody.

In a fifth embodiment a method is provided for the detection of a polynucleotide that encodes a filamentous fungal cotA in a biological sample. The method includes, but is not limited to, the following steps: (a) hybridizing, under moderate stringency, to a nucleic acid material of said biological sample, a polynucleotide fragment derived from any one of the sequences identified as SEQ ID NOs:1, 3 or 5, the fragment having a length of between about 15 and 250 nucleotides, thereby forming a hybridization complex; and (b) detecting said hybridization complex; wherein the presence of said hybridization complex correlates with the presence of a polynucleotide encoding the cotA protein in said biological sample. In a first aspect of this embodiment, the fragment is between 15 and 30 nucleotides in length. In another aspect, the fragment is between 30 and 100 nucleotides in length. In yet another aspect, the fragment is between 100 and 200 nucleotides in length, more preferred is a fragment between 200 and 250 nucleotides in length. In a final aspect, the fragment is about 241 nucleotides in length. In a second aspect of this embodiment, the biological sample is a filamentous fungal cell lysate. In third aspect of this embodiment, an agonist of cotA protein is identified. The method comprises the steps of (a) transfecting a fungal host cell with a polynucleotide that encodes a cotA protein; (b) inducing the expression of cotA; (c) contacting a test compound with the so induced fungal host cell, (d) measuring the effect of the test compound on the growth of the induced fungal cell; and (e) identifying the test compound as a candidate compound if it modulates the growth of the fungal cell beyond a selected threshold level.

In a final embodiment of this invention, a method of inducing a compact growth morphology of a filamentous fungal host cell is provided. In a preferred aspect of this embodiment, the fungal cell is a member of the *Trichoderma* genus, most preferred is *Trichoderma reesei*. In a more preferred aspect of this embodiment, the fungal cell is a member of the *Aspergillus* genus. In a most preferred aspect, the fungal cell is a *A. niger* cell. The method comprises the steps of transfecting said fungal host cell with a cotA polynucleotide or a fragment thereof operably linked to an inducible promoter, and exposing the transfected fungal host cell to a compound that induces expression of the cotA polynucleotide. In another preferred aspect of this embodiment, the cotA polynucleotide is as shown in any one of SEQ ID NOs:1, 3, 5, 13 or 14. In a particularly preferred aspect of this embodiment, the cotA polynucleotide is in the antisense orientation. In another particularly preferred aspect, the promoter is inducible by maltose.

BRIEF DESCRIPTION OF THE DRAWINGS

FIG. 1 is the nucleic acid sequence of the truncated *Aspergillus niger* cotA of this invention (SEQ ID NO:1).

FIG. 2 shows the deduced amino acid sequence of the truncated *Aspergillus niger* cotA of this invention (SEQ ID NO:2).

FIG. 3 is the nucleic acid sequence of the truncated *Aspergillus nidulans* cotA of this invention (SEQ ID NO:3).

FIG. 4 shows the deduced amino acid sequence of the truncated *Aspergillus nidulans* cotA of this invention (SEQ ID NO:4).

FIG. 5 is the nucleic acid sequence for an internal cotA fragment from *Trichoderma reesei* (SEQ ID NO:5).

FIG. 6 is the deduced amino acid sequence for the internal cotA fragment from *Trichoderma reesei* (SEQ ID NO:6).

Figure 7B:
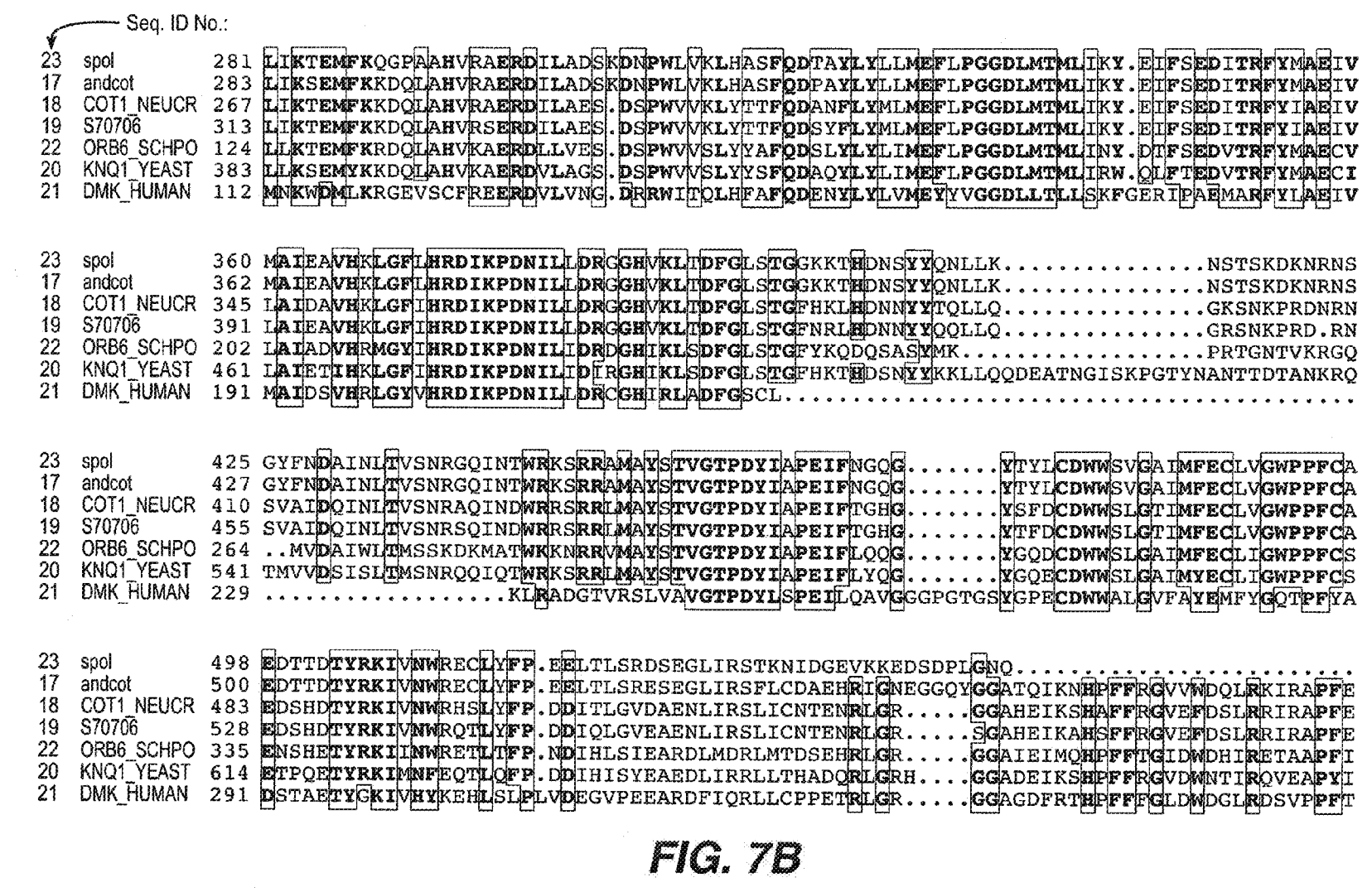

FIGS. 7A-C are a sequence alignment of cotA and related kinases. spo1 is the truncated cotA of *Aspergillus niger*. and-cot is the full length cotA from *Aspergillus nidulans*. COT1-NEUCR is the full length cot-1 from *Neurospora crassa*. S70706 is from *Colletotrichum trifolii*. KNQ1_YEAST is from *S. cerevisiae*. DMK_HUMAN is human myotonic dystrophy kinase.

FIG. 8A is a schematic of the integration of the expression vector, pSMB5, into the cotA locus of *Aspergillus niger*. FIG. 8B is a schematic of the locus after transformation.

FIG. 11 is the nucleic acid sequence of the full length cotA from *Aspergillus niger* (SEQ ID NO: 13). All introns are underlined. The start codon is in bold type. The functional truncated cotA gene ends at the italicized, underlined codon and is at the beginning of the second intron. The stop codon for the full-length cotA is shown in bold type.

FIG. 12 is the nucleic acid sequence of the full length cotA from *Aspergillus nidulans* (SEQ ID NO: 14).

FIG. 13 is a 269 bp probe from *Aspergillus niger* (SEQ ID NO:15).

FIG. 14 is the deduced amino acid sequence of the full-length *Aspergillus niger* cotA of this invention (SEQ ID NO:16).

DETAILED DESCRIPTION OF THE INVENTION

Figure 9A:
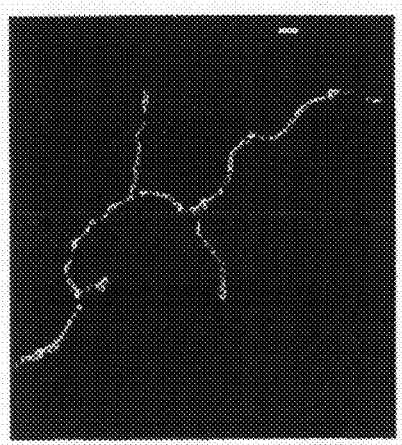
FIG. 9. Comparison of wt and glaAp-cotA strains on a variety of non-repressing (maltose) and repressing (xylose) carbon sources. Grown until same morphological age then stained with calcofluor. Bands=10 μm. YEPX Yeast Extract, Peptone and Xylose. YEPD Yeast Extract, Peptone and Glucose.

Many proteins and other compounds with industrial or pharmaceutical use, e.g., cellulases, proteases, lipases, xylanases, are produced in filamentous fungal cell cultures. An ongoing problem is that as the fungal cells divide and the culture expands, the number of cells in the culture make the culture viscous. In a continuous culture, oxygen and other nutrients do not mix as readily and are therefore unavailable for all the cells. In a batch culture, nutrients are exhausted at a faster rate as the culture expands. In both cases, the growth of the culture as well as the production of the desired protein reaches a plateau and begins to drop. It has been found that transforming filamentous fungal cells with cotA-encoding nucleic acids under the control of a regulatable promoter causes the transformed cells to reduce the rate of growth when in the presence of a compound that regulates the promoter. Transformation can occur with the cotA-encoding nucleic acid integrating in the cotA locus or ectopically. The reduced growth phenotype is seen in both instances. Without being held to any theory, it is believed that if integration occurs in the cotA locus, expression of wild type cotA is under the control of the heterologous and regulatable promoter and becomes inducible.

Fungal protein synthesis is located at the fungal growing tips. Increasing the number of growing tips by isolating hyperbranching mutants has benefits in fermentation. The compact morphology seen in hyperbranching mutants such as cot-1 would be useful in fungal fermentations where reduced viscosity could allow better fermentation performance. Not to be limited by theory, it is believed that the low viscosity of the fermenation mixture allows for better oxygenation of the media, which in turn enhances cell protein production.

A temperature sensitive cotA mutant may be created in various ways. For example, putting the cotA gene under a temperature sensitive promoter or creating a temperature sensitive cotA mutant in the filamentous fungi cotA homolog similar to the *N. crassa* cot-1 variant would be especially desirable. In an embodiment the filamentous fungi cotA homolog has been altered to have a substitution corresponding to the histidine to arginine substitution found in the *N. crassa* cot-1 variant. Thus, a temperature sensitive mutant that produces a hyperbranching phenotype with a compact morphology at a higher temperature is particularly desirable.

In one embodiment the endogenous cotA gene is replaced with a temperature sensitive cotA mutant having a substitution at the histidine residue that corresponds H352 in *N. crassa*. In one aspect the alteration is a substitution of the histidine to arginine (as found in the temperature sensitive *N. crassa* cot-1 variant). Thus, once the temperature sensitive cotA mutant has integrated into the host genome by homologous recombination it will be under the regulation of the endogenous cotA control sequences.

The ability of cotA mutant to effect protein secretion may be examined by growing the cotA mutant on petri dishes with starch as the sole carbon source. Manipulation of the expression of the cotA gene product would have utility in increasing heterologous protein secretion.

I. DEFINITIONS

Unless defined otherwise, all technical and scientific terms used herein have the same meaning as commonly understood by one of ordinary skill in the art to which this invention belongs. All references are incorporated by reference for all purposes. Although any methods and materials similar or equivalent to those described herein can be used in the practice or testing of the present invention, the preferred methods and materials are described. For purposes of the present invention, the following terms are defined below.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides. A cotA polypeptide includes, but is not limited to, a polypeptide encoded by the cotA polynucleotides of this invention. Specifically, cotA polypeptides or proteins encompass *Aspergillus* and *Trichoderma* cotA full length proteins, including, but not limited to, signal or leader sequences, mature proteins and fragments thereof.

As used herein, the term "overexpressing" when referring to the production of a protein in a host cell means that the protein is produced in greater amounts than its production in its naturally occurring environment.

As used herein, the phrase "protein associated with hyphal growth" refers to a protein which is capable of modulating hyphal growth in fungus. Illustrative of such proteins are the cotA proteins disclosed herein.

The term "nucleic acid molecule" includes RNA, DNA and cDNA molecules. It will be understood that, as a result of the degeneracy of the genetic code, a multitude of nucleotide sequences encoding a given proteins such as cotA may be produced. The present invention contemplates every possible variant nucleotide sequence, encoding cotA, all of which are possible given the degeneracy of the genetic code. A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in fungal cells and where expression of the selectable marker confers to cells containing the expressed gene the ability to grow in the presence of a corresponding selective agent.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene or nucleic acid sequence. In general, the transcriptional and translational regulatory sequences include, but are not limited to, promoter sequences, ribosomal binding sites, transcriptional start and stop sequences, translational start and stop sequences, and enhancer or activator sequences.

A "regulatable promoter" refers to a promoter that effects its regulatory control over a nucleic acid sequence under specific environmental conditions. For example, an inducible promoter is one that causes expression of the operably linked polynucleotide under certain environmental conditions, for example, blue light inducible promoters (bli-4), and copper metallothionein gene (cmt). In a more specific example, the glucoamylase A promoter (glaAp) induces expression in the presence of maltose.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Antisense" refers to sequences of nucleic acids that are complementary to the coding mRNA nucleic acid sequence of a gene. A nucleotide sequence linked to a promoter in an "antisense orientation" is linked to the promoter such that an RNA molecule complementary to the coding mRNA of the target gene is produced.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules that encode cotA or an analog or homologue thereof will hybridize, under moderate to high stringency conditions to any one of the sequences provided herein as SEQ ID NO:1, 3, 5, 13 or 14. However, in some cases a cotA-encoding nucleotide sequence is employed that possesses a substantially different codon usage, while the protein encoded by the cotA-encoding nucleotide sequence has the same or substantially the same amino acid sequence as the native protein. For example, the coding sequence may be modified to facilitate faster expression of cotA in a particular prokaryotic or eukaryotic expression system, in accordance with the frequency with which a particular codon is utilized by the host.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$-5° C. (5° below the $T_m$ of the probe); "high stringency" at about 5-10° below the $T_m$; "intermediate stringency" at about 10-20° below the $T_m$ of the probe; and "low stringency" at about 20-25° below the $T_m$. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al, 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "% homology" is used interchangeably herein with the term "% identity" herein and refers to the level of nucleic acid or amino acid sequence identity between the nucleic acid sequence that encodes cotA or the cotA amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for cotA, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See, also, Altschul, S. F. et al., 1990 and Altschul, S. F. et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In one exemplary approach, sequence extension of a nucleic acid encoding cotA may be may be carried out using conventional primer extension procedures as described in Sambrook et al., supra, to detect cotA precursors and processing intermediates of mRNA that may not have been reverse-transcribed into cDNA and/or to identify ORFs that encode a full length protein.

A nucleotide sequence encoding a cotA-type polypeptide, e.g., cot1 from *Neurospora crassa*, can also be used to construct hybridization probes for mapping the gene which encodes a cotA polypeptide and for further genetic analysis. Screening of a cDNA or genomic library with the selected probe may be conducted using standard procedures, such as described in Sambrook et al., 1989). Hybridization conditions, including moderate stringency and high stringency, are provided in Sambrook et al., supra.

The probes or portions thereof may also be employed in PCR techniques to generate a pool of sequences for identification of closely related cotA sequences. When cotA sequences are intended for use as probes, a particular portion of a cotA encoding sequence, for example a highly conserved portion of the coding sequence may be used.

For example, a cotA nucleotide sequence may be used as a hybridization probe for a cDNA library to isolate genes, for example, those encoding naturally-occurring variants of cotA from other filamentous fungal species, which have a desired level of sequence identity to any one of the cotA nucleotide sequences disclosed in FIG. 1, 3, 5, 11 or 12 (SEQ ID NO:1, 3, 5, 13 or 14, respectively). Exemplary probes have a length of about 20 to about 50 bases but can go as long as 250 bp.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome that is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "expression" refers to the process by which a polypeptide is produced based on the nucleic acid sequence of a gene. The process includes both transcription and translation. It follows that the term "cotA expression" refers to transcription and translation of the cotA gene, the products of which include precursor RNA, mRNA, polypeptide, post-translation processed polypeptide, and derivatives thereof, including cotA homologs from other fungal species. By way of example, assays for cotA expression include examination of fungal colonies when exposed to the appropriate conditions, western blot for cotA protein, as well as northern blot analysis and reverse transcriptase polymerase chain reaction (RT-PCR) assays for cotA mRNA.

"Alternative splicing" is a process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

By "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as filamentous fungal, yeast, plant, insect, amphibian, or mammalian cells. In general, host cells are filamentous fungal cells. Specifically, the present invention find *A. nidulans, A. niger* and *T. reesei* cells advantageous.

The terms "isolated" or "purified" as used herein refer to a nucleic acid or polypeptide that is removed from at least one component with which it is naturally associated.

As used herein, the terms "active" and "biologically active" refer to a biological activity associated with a particular protein, such as the enzymatic activity associated with a kinase. It follows that the biological activity of a given protein refers to any biological activity typically attributed to that protein by those of skill in the art.

The phrase "slowed growth morphology" means the cells exhibit a more slowly growing phenotype than wild type cells. This is evidenced by a more compact colony appearance on solid growth medium. This morphology may be accompanied by hyphal hyper-branching.

II. TARGET ORGANISMS

In this invention, the source of the polynucleotides that encode cotA is a filamentous fungus. As well as being the source, in a preferred embodiment, the host cell is also a filamentous fungus cell. Filamentous fungi include all filamentous forms of the subdivision Eumycota and Oomycota. The filamentous fungi are characterized by vegetative mycelium composed of chitin, cellulose, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Aspergillus, Humicola* and *Trichoderma*. In one embodiment, the filamentous fungal parent cell is an *Aspergillus niger*, or an *Aspergillus nidulans* cell. In a aspect, the parent cell is an *Aspergillus niger* cell. In a second aspect, the parent cell is an *Aspergillus nidulans* cell. In third aspect, the filamentous fungal parent cell is a *Trichoderma reesei* cell. In a fourth aspect, the filamentous fungal parent cell is *Humicola grisea*.

III. METHODS OF IDENTIFYING NOVEL SEQUENCES

It has been discovered that cotA-encoding polynucleotides share significant identity at the 3' terminus. This region encodes the catalytic region of cotA. Thus, it is expected that cotA homologs from other fungal species may be found through searching fungal genomes for homologous sequences or by degenerate PCR cloning of the conserved region. Open reading frames (ORFs) within a fungal genome are analyzed following full or partial sequencing of the target organism (in this case, fungal) genome and are further analyzed using sequence analysis software, and by determining homology to known sequences in databases (public/private). Sequence searching and comparison techniques are well known and readily available via the World Wide Web.

In a one aspect of this invention, cotA homologs are discovered through degenerate PCR cloning. Useful primers include, but are not limited to, 5'-GA T/C AT T/C AA A/G CCNGA T/C AA-3' (SEQ ID NO:7) and 5'-TCNGGNGC G/T/A AT A/G TA A/G TC-3' (SEQ ID NO:8). Other primers will be apparent to those of skill in the art upon review of the sequences listed in FIG. 7. PCR conditions to optimize hybridization of degenerate primers to genomic DNA and subsequent amplification are well within the purview of those of skill in the art. Such conditions may be found in Ausubel and/or Sambrook.

Although genomic sequences can be discovered directly through PCR cloning, in a preferred method, a probe consisting of a partial polynucleotide sequence is generated via PCR cloning. Typically this probe is less than 1000 base pairs, more preferably less than 750 base pairs, even more preferably less than 500 bp and most preferably less than 250 base pairs. In a particularly preferred embodiment, the probe is from about 241 to 269 base pairs in length (FIG. 13 (SEQ ID NO:15) and corresponds approximately to residues 1144-1405 of the *N. crassa* cot-1 sequence.

IV. COTA POLYPEPTIDES AND NUCLEIC ACID MOLECULES ENCODING COTA

A. cotA Nucleic Acids

The nucleic acid molecules of the present invention include a coding sequence for *A. niger* cotA presented herein as SEQ. ID. NO: 13 or *A. nidulans* presented herein as SEQ. ID. NO: 14, naturally occurring allelic and splice variants, nucleic acid fragments, and biologically active (functional) derivatives thereof, such as, amino acid sequence variants of the native molecule and sequences which encode fusion proteins.

The nucleic acid molecules of the present invention include a partial native coding sequence for cotA presented herein as SEQ. ID. NO:1, and homologues thereof in other species (for example, SEQ ID NO:3 (cotA from *A. nidulans*) and SEQ ID NO:5 (cotA from *T. reesei*)), naturally occurring allelic and splice variants, nucleic acid fragments, and biologically active (functional) derivatives thereof, such as, amino acid sequence variants of the native molecule and sequences which encode fusion proteins. The sequences, both full length and partial sequences, are collectively referred to herein as "cotA-encoding nucleic acid sequences".

A cotA nucleic acid sequence of this invention may be a DNA or RNA sequence, derived from genomic DNA, cDNA, mRNA, or may be synthesized in whole or in part. The DNA may be double-stranded or single-stranded and if single-stranded may be the coding strand or the non-coding (antisense, complementary) strand. The nucleic acid sequence may be cloned, for example, by isolating genomic DNA from an appropriate source, and amplifying and cloning the sequence of interest using a polymerase chain reaction (PCR). Alternatively, nucleic acid sequences may be synthesized, either completely or in part, especially where it is desirable to provide host-preferred sequences for optimal expression. Thus, all or a portion of the desired structural gene (that portion of the gene which encodes a polypeptide or protein) may be synthesized using codons preferred by a selected host, e.g., *Aspergillus niger, Aspergillus nidulans* or *Trichoderma reesei*.

Due to the inherent degeneracy of the genetic code, nucleic acid sequences other than the native form that encode substantially the same or a functionally equivalent amino acid sequence may be used to clone and/or express cotA-encoding nucleic acid sequences. Thus, for a given cotA-encoding nucleic acid sequence, it is appreciated that, as a result of the degeneracy of the genetic code, a number of coding sequences can be produced that encode a protein having the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the nucleic acid sequence variants covered by the present invention. Any and all of these sequence variants can be utilized in the same way as described herein for the native form of a cotA-encoding nucleic acid sequence.

A "variant" cotA-encoding nucleic acid sequence may encode a "variant" cotA amino acid sequence which is altered by one or more amino acids from the native polypeptide sequence, both of which are included within the scope of the invention. Similarly, the term "modified form of", relative to cotA, means a derivative or variant form of the native cotA protein-encoding nucleic acid sequence or the native cotA amino acid sequence.

Similarly, the polynucleotides for use in practicing the invention include sequences which encode native cotA proteins and splice variants thereof, sequences complementary to the native protein coding sequence, and novel fragments of cotA encoding polynucleotides.

In one general embodiment, a cotA-encoding nucleotide sequence has at least 70%, preferably 80%, 85%, 90%, 95%, 98%, or more sequence identity to any one of the cotA coding sequences presented herein as SEQ ID NOs:1, 3 or 5.

In another embodiment, a cotA-encoding nucleotide sequence will hybridize under moderate to high stringency conditions to a nucleotide sequence that encodes a cotA protein. In a related embodiment, a cotA-encoding nucleotide sequence will hybridize under moderate to high stringency conditions to any one of the nucleotide sequences presented as SEQ ID NOs:1, 3 or 5.

It is appreciated that some nucleic acid sequence variants that encode cotA may or may not selectively hybridize to the parent sequence. By way of example, in situations where the coding sequence has been optimized based on the degeneracy of the genetic code, a variant coding sequence may be produced that encodes a cotA protein, but does not hybridize to a native cotA-encoding nucleic acid sequence under moderate to high stringency conditions. This would occur, for example, when the sequence variant includes a different codon for each of the amino acids encoded by the parent nucleotide.

As will be further understood by those of skill in the art, in some cases it may be advantageous to produce nucleotide sequences possessing non-naturally occurring codons. Codons preferred by a particular eukaryotic host (Murray, E. et al., 1989) can be selected, for example, to increase the rate of cotA protein expression or to produce recombinant RNA transcripts having desirable properties, such as a longer half-life, than transcripts produced from the naturally occurring sequence. Hence, a native cotA-encoding nucleotide sequence may be engineered in order to alter the coding sequence for a variety of reasons, including but not limited to, alterations which modify the cloning, processing and/or expression of the cotA protein by a cell.

A cotA-encoding nucleotide sequence may be engineered in order to alter the cotA coding sequence for a variety of reasons, including but not limited to, alterations which modify the cloning, processing and/or expression of cotA by a cell.

Particularly preferred are nucleic acid substitutions, additions, and deletions that are silent such that they do not alter the properties or activities of the native polynucleotide or polypeptide.

The variations can be made using methods known in the art such as oligonucleotide-mediated (site-directed) mutagenesis, alanine scanning, and PCR mutagenesis. Site-directed mutagenesis [Carter et al., 1986; Zoller et al., 1987], cassette mutagenesis [Wells et al., 1985], restriction selection mutagenesis [Wells et al., 1986] or other known techniques can be performed on the cloned DNA to produce the cotA polypeptide-encoding variant DNA.

However, in some cases it may be advantageous to express variants of cotA which lack the properties or activities of the native cotA polynucleotide or polypeptide. In such cases, mutant or modified forms of the native cotA-encoding nucleic acid sequence may be generated using techniques routinely employed by those of skill in the art. For example, in a preferred embodiment, a fragment of a cotA-encoding polynucleotide is transfected into a fungal host cell. The manufacture of fragments of full length genomic and/or coding sequences is well within the skill of one in the art.

B. cotA Polypeptides

In one embodiment, the invention provides a truncated cotA polypeptide, having a polypeptide sequence comprising the sequence presented in FIG. 2 (SEQ ID NO:2). In another embodiment, a cotA polypeptide of the invention can be the mature cotA polypeptide, part of a fusion protein or a fragment or variant of the cotA polypeptide.

In another embodiment, the invention provides a truncated cotA polypeptide, having a polypeptide sequence comprising the sequence presented in FIG. 4 (SEQ ID NO:4). In another embodiment, a cotA polypeptide of the invention can be the mature cotA polypeptide, part of a fusion protein or a fragment or variant of the cotA polypeptide.

In a third embodiment, the invention provides a truncated cotA polypeptide, having a polypeptide sequence comprising the sequence presented in FIG. 6 (SEQ ID NO:6). In another embodiment, a cotA polypeptide of the invention can be the mature cotA polypeptide, part of a fusion protein or a fragment or variant of the cotA polypeptide.

Ordinarily, a cotA polypeptide of the invention comprises a region having at least 80, 85, 90, 95, 98% or more sequence identity to any one of the cotA polypeptide sequences of FIG. 2, 4 or 6 (SEQ ID NO:2, 4 or 6, respectively), using a sequence alignment program, as detailed herein.

Typically, a "modified form of" a native cotA protein or a "variant" cotA protein has a derivative sequence containing at least one amino acid substitution, deletion or insertion, respectively.

Fragments and variants of any one of the cotA polypeptide sequences of FIG. 2, 4 or 6 (SEQ ID NOs:2, 4 or 6, respectively), are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human. In this aspect, the invention includes (i) fragments of cotA, preferably at least about 20-100 amino acids in length, more preferably about 100-200 amino acids in length, and (ii) a pharmaceutical composition comprising cotA. In various embodiments, the fragment corresponds to the N-terminal domain of cotA or the C-terminal domain of cotA.

cotA polypeptides of the invention also include polypeptides that vary from any one of the cotA polypeptide sequences of FIG. 2, 4 or 6 (SEQ ID NO:2, 4 or 6, respectively). These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g. by a standard Dayhoff frequency exchange matrix or BLOSUM matrix). (See generally, Doolittle, R. F., 1986.)

A "non-conservative substitution" refers to the substitution of an amino acid in one class with an amino acid from another class.

cotA polypeptide variants typically exhibit the same qualitative biological activity as the naturally-occurring analogue, although variants also are selected to modify the characteristics of the cotA polypeptide, as needed. For example, glycosylation sites, and more particularly one or more O-linked or N-linked glycosylation sites may be altered or removed. Those skilled in the art will appreciate that amino acid changes may alter post-translational processes of the cotA polypeptide, such as changing the number or position of glycosylation sites or altering the membrane anchoring characteristics.

Also included within the definition of cotA polypeptides are other related cotA polypeptides. Thus, probe or degenerate polymerase chain reaction (PCR) primer sequences may be used to find other related polypeptides. Useful probe or primer sequences may be designed to: all or part of the cotA polypeptide sequence, or sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of cotA polypeptides are also included within the scope of this invention. For example, the invention provides cotA polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes are used to remove any additional amino acids from the mature protein.

C. Anti-cotA Antibodies.

The present invention further provides anti-cotA antibodies. The antibodies may be polyclonal, monoclonal, humanized, bispecific or heteroconjugate antibodies.

Methods of preparing polyclonal antibodies are known to the skilled artisan. The immunizing agent may be a cotA polypeptide or a fusion protein thereof. It may be useful to conjugate the antigen to a protein known to be immunogenic in the mammal being immunized. The immunization protocol may be determined by one skilled in the art based on standard protocols or routine experimentation. Alternatively, the anti-cotA antibodies may be monoclonal antibodies. Monoclonal antibodies may be produced by cells immunized in an animal or using recombinant DNA methods. [See, e.g., Kohler et al., 1975; U.S. Pat. No. 4,816,567]. Antibodies to proteins have many uses well known to those of skill in the art. Here, it is envisioned that antibodies to cotA are useful as a component of staining reagents to determine the expression of cotA in fungal host cells among other uses that will be apparent to those of skill.

V. EXPRESSION OF RECOMBINANT cotA AND cotA FRAGMENTS

This invention provides filamentous fungal host cells which have been transduced, transformed or transfected with an expression vector comprising a cotA-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell line is transfected with an expression vector having a promoter or biologically active promoter fragment or one or more (e.g., a series) of enhancers which functions in the host cell line, operably linked to a DNA segment encoding cotA, such that cotA is expressed in the cell line. In a preferred embodiment, the DNA sequences encode a partial cotA coding sequence. In another preferred embodiment, the promoter is a regulatable one.

A. Nucleic Acid Constructs/Expression Vectors.

Natural or synthetic polynucleotide fragments encoding cotA ("cotA-encoding nucleic acid sequences") may be incorporated into heterologous nucleic acid constructs or vectors, capable of introduction into, and replication in, a filamentous fungal cell. The vectors and methods disclosed herein are suitable for use in host cells for the expression of cotA. Any vector may be used as long as it is replicable and viable in the cells into which it is introduced. Large numbers of suitable vectors and promoters are known to those of skill in the art, and are commercially available. Appropriate cloning and expression vectors for use in filamentous fungal cells are also described in Sambrook et al., 1989, and Ausubel F M et al., 1989, expressly incorporated by reference herein. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Appropriate vectors are typically equipped with a selectable marker-encoding nucleic acid sequence, insertion sites, and suitable control elements, such as termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothienein promoter that can upregulated by addition of certain metal salts. In one embodiment of this invention, glaA promoter is used. This promoter is induced in the presence of maltose. In a preferred embodiment, a promoter that is induced by maltose is used. Such promoters are well known to those of skill in the art.

The choice of the proper selectable marker will depend on the host cell, and appropriate markers for different hosts are well known in the art. Typical selectable marker genes encode proteins that (a) confer resistance to antibiotics or other toxins, for example, ampicillin, methotrexate, tetracycline, neomycin (Southern and Berg, J., 1982), mycophenolic acid (Mulligan and Berg, 1980), puromycin, zeomycin, or hygromycin (Sugden et al., 1985). In a preferred embodiment, PyrG is used as a selectable marker.

A selected cotA coding sequence may be inserted into a suitable vector according to well-known recombinant techniques and used to transform a cell line capable of cotA expression. Due to the inherent degeneracy of the genetic code, other nucleic acid sequences which encode substantially the same or a functionally equivalent amino acid sequence may be used to clone and express cotA, as further detailed above. Therefore it is appreciated that such substitutions in the coding region fall within the sequence variants covered by the present invention. Any and all of these sequence variants can be utilized in the same way as described herein for a parent cotA-encoding nucleic acid sequence.

Once the desired form of a cotA nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

The present invention also includes recombinant nucleic acid constructs comprising one or more of the cotA-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for cotA, or a variant, fragment or splice variant thereof: (i) in isolation; (ii) in combination with additional coding sequences; such as fusion protein or signal peptide coding sequences, where the cotA coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cotA coding sequence is a heterologous gene.

A heterologous nucleic acid containing the appropriate nucleic acid coding sequence, as described above, together with appropriate promoter and control sequences, may be employed to transform filamentous fungal cells to permit the cells to express cotA.

In one aspect of the present invention, a heterologous nucleic acid construct is employed to transfer a cotA-encoding nucleic acid sequence into a cell in vitro, with established cell lines preferred. Preferably, cell lines that are to be used as production hosts have the nucleic acid sequences of this invention stably integrated. Integration preferably occurs in the cotA locus but ectopic integration is useful as well. It follows that any method effective to generate stable transformants may be used in practicing the invention.

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Animal Cell Culture" (R. I. Freshney, ed., 1987); "Current Protocols in Molecular Biology" (F. M. Ausubel et al., eds., 1987); and "Current Protocols in Immunology" (J. E. Coligan et al., eds., 1991). All patents, patent applications, articles and publications mentioned herein, both supra and infra, are hereby expressly incorporated herein by reference.

B. Host Cells and Culture Conditions for Regulatable Expression.

Thus, the present invention provides cell lines comprising cells which have been modified, selected and cultured in a manner effective to result in regulatable expression of cotA relative to the corresponding non-transformed parental cell line.

Examples of parental cell lines which may be treated and/or modified for regulatable cotA expression include, but are not limited to filamentous fungal cells. Examples of appropriate primary cell types for use in practicing the invention include, but are not limited to, *Aspergillus* and *Trichoderina*.

cotA expressing cells are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of cotA expression are achieved.

Preferred culture conditions for a given cell line may be found in the scientific literature and/or from the source of the cell line such as the American Type Culture Collection. Typically, after cell growth has been established, the cells are exposed to conditions effective to cause or inhibit the expression of cotA and truncated cotA.

In the preferred embodiments, where a cotA coding sequence is under the control of an inducible promoter, the inducing agent, e.g. a carbohydrate, metal salt or antibiotics, is added to the medium at a concentration effective to induce cotA expression.

C. Introduction of a cotA-Encoding Nucleic Acid Sequence into Host Cells.

The invention further provides cells and cell compositions which have been genetically modified to comprise an exogenously provided cotA-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above. In a preferred embodiment, a plasmid is used to transfect a filamentous fungal cell.

Various methods may be employed for delivering an expression vector into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; and the like. In addition, heterologous nucleic acid constructs comprising a cotA-encoding nucleic acid sequence can be transcribed in vitro, and the resulting RNA introduced into the host cell by well-known methods, e.g., by injection.

In a preferred embodiment, the expression vector comprising a truncated cotA and an appropriate promoter is constructed such that the promoter and cotA sequence integrates in the cotA locus. This is accomplished via a single recombination event within the cotA locus. In a more preferred embodiment, the expression vector is constructed such that a double recombination event occurs. The vector comprises a stretch of nucleic acid that is complementary to a stretch of nucleic acid in the cotA locus upstream from the cotA coding sequence. The other site of complementary DNA occurs in the coding region. Upon integration, two crossover events occur so that only the appropriate promoter and the truncated cotA sequence are inserted into the cotA locus instead of the entire expression vector.

Following introduction of a heterologous nucleic acid construct comprising the coding sequence for cotA, the genetically modified cells can be cultured in conventional nutrient media modified as appropriate for activating promoters, selecting transformants or amplifying expression of a cotA-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the cotA-encoding nucleic acid sequence found in the heterologous nucleic acid construct.

VI. ANALYSIS OF COTA NUCLEIC ACIDS AND PROTEINS

In order to evaluate the expression of cotA by a cell line that has been transformed with a cotA-encoding nucleic acid construct, assays can be carried out at the protein level, the RNA level or by use of functional bioassays particular to growth characteristics of the transfected cell line.

By way of example, the production and/or expression of cotA may be measured in a sample directly, for example, by microscopic examination of transfected cells. Filamentous fungal cells that have been transfected with cotA under the control of an inducible promoter exhibit slowed and more compact growth compared to parental fungal cells when exposed to the compound that induces expression. Nucleic acid-based assays for determining the expression of cotA include, but are not limited to, northern blotting to quantitate the transcription of mRNA, dot blotting (DNA or RNA analysis), RT-PCR (reverse transcriptase polymerase chain reaction), or in situ hybridization, using an appropriately labeled probe (based on the nucleic acid coding sequence) and conventional Southern blotting.

Alternatively, protein expression, may be evaluated by immunological methods, such as immunohistochemical staining of cells, tissue sections or immunoassay of tissue culture medium, e.g., by western blot or ELISA. Such immunoassays can be used to qualitatively and quantitatively evaluate expression of cotA. The details of such methods are known to those of skill in the art and many reagents for practicing such methods are commercially available.

A purified form of cotA is typically used to produce either monoclonal or polyclonal antibodies specific to the expressed protein for use in various immunoassays. (See, e.g., Harlow and Lane, 1988). Exemplary assays include ELISA, competitive immunoassays, radioimmunoassays, western blot, indirect immunofluorescent assays and the like. In general, commercially available antibodies and/or kits may be used for the quantitative immunoassay of the expression level of known types of proteins.

VII. ISOLATION AND PURIFICATION OF RECOMBINANT COTA PROTEIN

In general, a cotA protein produced in a filamentous fungal cell is not secreted into the medium and therefore must be purified from cell lysates. This can be accomplished by techniques routine employed by those of skill in the art.

Typically, after removal of cell debris, the lysate comprising cotA protein is fractionated to segregate proteins having selected properties, such as binding affinity to particular binding agents, e.g., antibodies or receptors; or which have a selected molecular weight range, or range of isoelectric points.

Once expression of a given cotA protein is achieved, the cotA protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

VIII. UTILITY OF THE COTA POLYPEPTIDES AND NUCLEIC ACIDS OF THIS INVENTION

From the foregoing, it can be appreciated that cells transformed with cotA under the control of an inducible promoter grow more slowly in conditions in which cotA is expressed. By retarding the growth of fungal cell cultures, fermenter cultures of such cells can be maintained for longer periods of time. Because fermenter cultures are maintained for longer periods, expressed protein levels can be maintained for longer periods of time. Thus, elevated concentrations of expressed protein can be achieved. As would be obvious to one of skill, this would lead to lower production costs.

For production of a desired protein in a fungal host cell, an expression vector comprising at least one copy of nucleic acid encoding a desired protein is transformed into the recombinant host cell comprising nucleic acid encoding a protein associated with hyphal growth and cultured under conditions suitable for expression of the protein. Examples of desired proteins include enzymes such as hydrolases including proteases, cellulases, amylases, carbohydrases, and lipases; isomerases such as racemases, epimerases, tautomerases, or mutases; transferases, kinases and phophatases along with proteins of therapeutic value.

Thus, the present invention is particularly useful in enhancing the intracellular and/or extracellular production of proteins. The protein may be homologous or heterologous. Proteins that may produced by the instant invention include, but are not limited to, hormones, enzymes, growth factors, cytokines, antibodies and the like.

Enzymes include, but are not limited to, hydrolases, such as protease, esterase, lipase, phenol oxidase, permease, amylase, pullulanase, cellulase, glucose isomerase, laccase and protein disulfide isomerase.

Hormones include, but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 ($\alpha$ and $\beta$), IL-2 through IL-13) and the interferons ($\alpha$, $\beta$ and $\gamma$).

Human Interleukin-3 (IL-3) is a 15 kDa protein containing 133 amino acid residues. IL-3 is a species specific colony stimulating factor which stimulates colony formation of megakaryocytes, neutrophils, and macrophages from bone marrow cultures.

Antibodies include, but are not limited to, immunoglobulins from any species from which it is desirable to produce large quantities. It is especially preferred that the antibodies are human antibodies. Immunoglobulins may be from any class, i.e., G, A, M, E or D.

EXAMPLES

The following examples are submitted for illustrative purposes only and should not be interpreted as limiting the invention in any way.

Example 1

Isolation of a Truncated cotA Polynucleotide from *Aspergillus niger*

Based on an alignment of cot1 from *N. crassa*, TB3 (a Colletotrichum homologue), KNQ_1/Cbk1p, a related kinase in *S. cerevisiae*, and Homo sapiens DMK, degenerate oligonucleotides were designed against 2 conserved regions of the coding sequence.

```
                                           (SEQ ID NO: 7)
    DIKPDN (5' forward primer)
    5'-GA T/C AT T/C AA A/G CCNGA T/C AA-3'

(SEQ ID NO: 8)
    EPAIYD (3' reverse primer)
    5'-TCNGGNGC G/T/A AT A/G TA A/G TC-3'
```

Using routine PCR conditions and genomic *A. niger* DNA, a 241 internal fragment was produced. This fragment was sequenced and found to have closest homology to cot-1 of *N. crassa*. This fragment was used to probe digested *A. niger* genomic DNA on a Southern blot according to routine methods. A 6.5 kb band from a HindIII digest hybridized with the probe.

*A. niger* genomic DNA was digested with HindIII, recircularized and ligated. This circularized DNA was subjected to inverse PCR using oligonucleotides designed from the nucleotide sequence of the 241 bp region homologous to cot-1.

```
    INV3' (reverse primer)
    5'ACGTCGAGITCTTCAGC 3'      (SEQ ID NO: 9)

INV5' (forward primer)
    5'GCGATCAACCTGACAGT 3'      (SEQ ID NO: 10)
```

A 6.5 kb fragment produced from the inverse PCR reaction was inserted into the cloning vector pCR® 2.1. The resulting construct, pPOL, was sequenced. The sequence data allowed orientation of the *A. niger* cotA within the 6.5 kb fragment. The selected open reading frame of *A. niger* was aligned with related kinases (See FIG. 7).

As can be seen from FIG. 7, the 6.5 kb fragment contains an open reading frame of approximately 500 amino acids or of 10.5 kb. Alignment of the ORF of the *A. niger* homologue with cot-1 indicated that about 50 amino acids or 150 base pairs from the C or 3' terminal were missing from the coding region.

Example 2

Expression of Truncated *A. niger* cotA 1.4 kb of the 5' coding region of cotA under the control of the glaA promoter was inserted into the expression vector pGRT-pyrG1 (Ward, et al, *Appl Microbiol and Biotech*. 39:738-743 (1993)) to examine the effect of regulated expression of cotA on the growth morphology of *A. niger*. glaAp is induced by maltose and repressed by xylose. The resulting plasmid, pSMB5, was used to transform an *A. niger* pyrG-recipient. See FIG. 8 for schematic of transformation. Pyr+ transformants were selected on minimal medium with maltose as the sole carbon source and screened for growth morphology on xylose. Transformants that showed restricted growth on xylose but that grew well on maltose, were analyzed by Southern hybridization. In one colony of transformants (SMB540), integration of the plasmid occurred at the cotA locus, in others, ectopic integration took place.

Parental *A. niger* cotA strains were compared to strains carrying the glaAp-cotA fusion after growth on different C-sources, to regulate expression of glaAp. Morphological changes occurred only during repression of cotA expression, with YEPX more repressing than MM+1% xylose. When cotA+ and glaAp-cotA strains were grown on maltose (non-repressing) then no morphological difference was seen between the strains.

Example 3

Truncated cotA in the Antisense Orientation

To determine what effect disruption of cotA would have on the growth of *A. niger*, an *A. niger* strain was transformed with cotA under the control of glaAp as above, except the cotA sequence was in the antisense orientation.

Figure 9D:
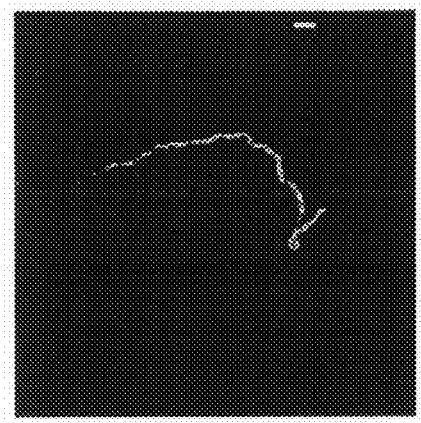
Figure 9B:
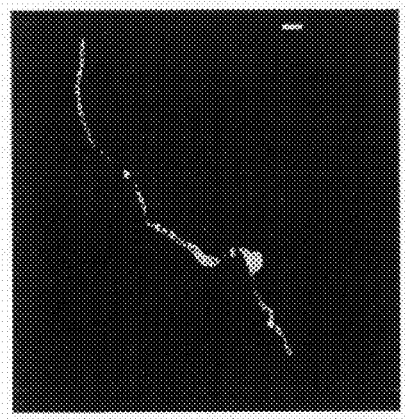
Figure 9E:
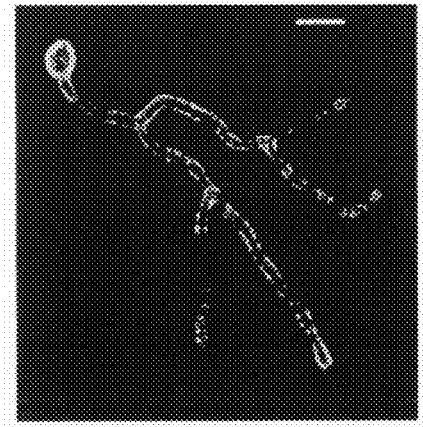
Figure 9C:
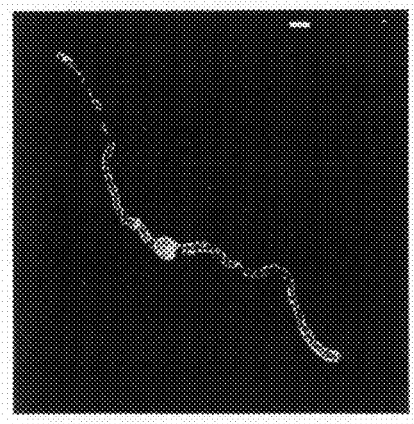
Figure 9F:
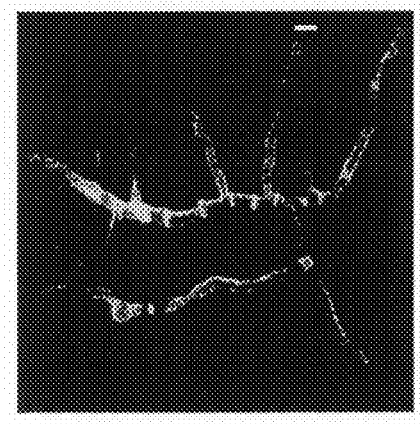
Figure 10A:
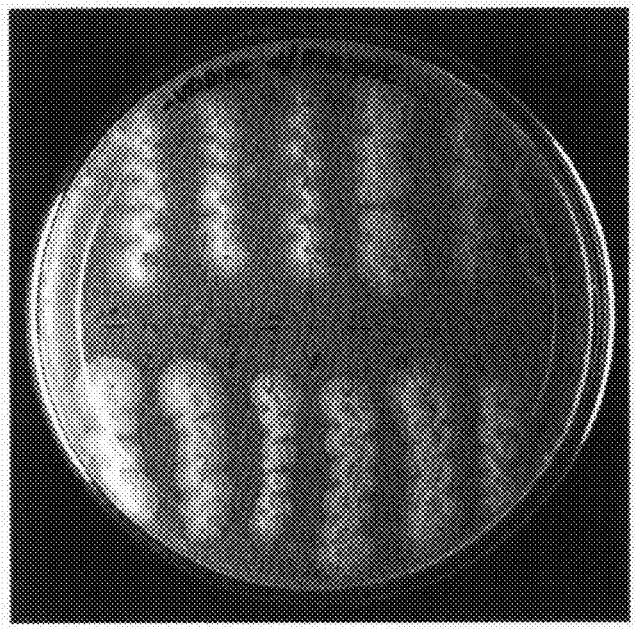
FIGS. 10A and 10B are photographs of *Aspergillus niger* transfected with cotA in the antisense orientation under the control of the glaA promoter. As can be seen, a slowed growth phenotype is observed when transformed cells are grown in the presence of xylose or maltose (FIGS. 10a and b).
Figure 10B:
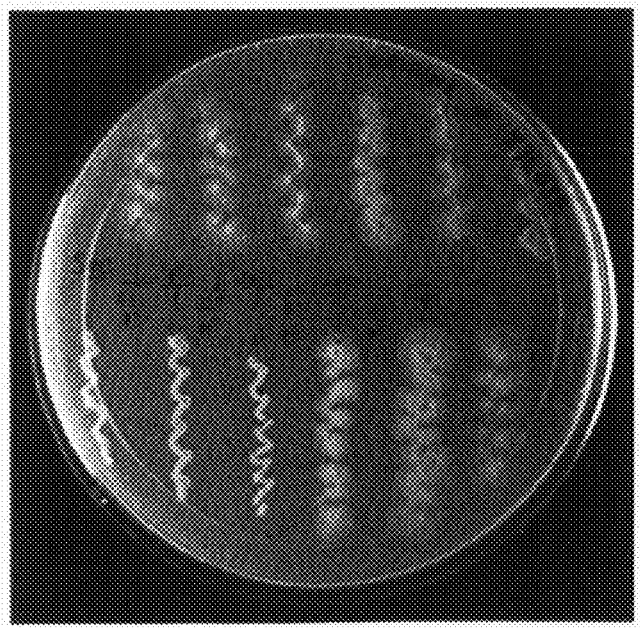

As can be seen in FIG. 9, the morphology of the transformants is very slow growing and compact with very long branches.

Example 4

Point Mutation in the cotA Locus

From the literature, it is known that in *N. crassa*, a single mutation in the cot-1 locus creates the temperature sensitive hyperbranching phenotype. In cot-1, a histidine naturally occurs at position 352 (see FIG. 7). The cot-1 mutation is caused by a switch to arginine at this position.

Site directed mutagenesis can be used to manufacture the same mutation in the cotA coding sequence of *A. niger*. Using techniques very similar to those described above, the cotA coding sequence with the point mutation as well as an inducible promoter can be integrated into the cotA locus or ectopically. It is expected that, when induced, the mutation will cause the slow growth morphology described above Example 5

Isolation of Truncated Cot-1 from *Trichoderma reesei*

Using degenerate PCR, a 264 base pair cot-1 nucleic acid sequence was isolated from genomic *T. reesei* genomic DNA. The forward primer was 5' GA T/C AT T/C AA A/G CC A/G/C/T GA A/C AA-3' (SEQ ID NO:11) and the reverse primer was 5' TC A/G/C/T GG A/C/G/T GC G/T AT A/G TA A/G TC-3' (SEQ ID NO:12).

The internal cot-1 fragment is shown in FIG. 5 (SEQ ID NO:5) and the translated sequence is shown in FIG. 6 (SEQ ID NO:6).

What is claimed is:

1. An isolated polynucleotide that encodes or is fully complementary to a sequence that encodes a cotA polypeptide having serine/threonine kinase activity selected from the group consisting of:
   a nucleic acid sequence that encodes or is fully complementary to a sequence that encodes a cotA polypeptide having at least 95% sequence identity to the amino acid sequence presented as SEQ ID NO:2 (FIG. 2),
   a nucleic acid sequence that encodes or is fully complementary to a sequence that encodes a cotA polypeptide having the amino acid sequence presented as SEQ ID NO:2 (FIG. 2), and
   the nucleic acid sequence presented as SEQ ID NO:1 (FIG. 1) or the full complement thereof.

2. An expression cassette comprising a promoter operatively linked to a polynucleotide of claim 1.

3. The expression cassette of claim 2, wherein the promoter is inducible.

4. The expression cassette of claim 3, wherein the promoter is selected from the group consisting of glucoamylase gene promoter, blue light inducible promoters (bli-4), and copper metallothionein gene (cmt) promoter.

5. The expression cassette of claim 4, wherein the promoter is the glucoamylase A (glaA) promoter.

6. An expression vector comprising the expression cassette of claim 2.

* * * * *